United States Patent
Ida

(10) Patent No.: US 9,001,057 B2
(45) Date of Patent: Apr. 7, 2015

(54) MEASUREMENT DEVICE

(75) Inventor: Yoshihiko Ida, Kyoto (JP)

(73) Assignee: Horiba, Ltd. (JP)

( * ) Notice: Subject to any disclaimer, the term of this patent is extended or adjusted under 35 U.S.C. 154(b) by 123 days.

(21) Appl. No.: 13/410,925

(22) Filed: Mar. 2, 2012

(65) Prior Publication Data
US 2012/0223902 A1 Sep. 6, 2012

(30) Foreign Application Priority Data

Mar. 3, 2011 (JP) ................................. 2011-047021
Mar. 3, 2011 (JP) ................................. 2011-047026

(51) Int. Cl.
*G09G 5/00* (2006.01)
*G01N 33/18* (2006.01)

(52) U.S. Cl.
CPC ...................................... *G01N 33/18* (2013.01)

(58) Field of Classification Search
CPC . G06F 3/0481; G06F 3/0484; G06F 3/04845; G06F 3/0485; G06F 3/0486; G06F 3/0487; G06F 3/0488; G01N 33/18
USPC ................. 345/173; 178/18.03; 715/863, 864
See application file for complete search history.

(56) References Cited

U.S. PATENT DOCUMENTS

| | | | | |
|---|---|---|---|---|
| 8,170,620 | B2* | 5/2012 | Kim | 455/566 |
| 8,199,125 | B2* | 6/2012 | Misawa et al. | 345/173 |
| 8,332,771 | B2* | 12/2012 | Inaba | 715/769 |
| 8,416,346 | B2* | 4/2013 | Bae et al. | 348/511 |
| 2004/0046796 | A1* | 3/2004 | Fujita | 345/767 |
| 2007/0222769 | A1* | 9/2007 | Otsuka et al. | 345/173 |
| 2008/0201637 | A1 | 8/2008 | Shirasaki | |
| 2008/0225014 | A1* | 9/2008 | Kim | 345/173 |
| 2009/0046075 | A1* | 2/2009 | Kim et al. | 345/173 |
| 2010/0004029 | A1* | 1/2010 | Kim | 455/566 |
| 2010/0079672 | A1* | 4/2010 | Bae et al. | 348/565 |

(Continued)

FOREIGN PATENT DOCUMENTS

JP 01142818 A 6/1989
JP 2004-325077 A 11/2004

(Continued)

OTHER PUBLICATIONS

The extended European Search Report for European Patent Application No. 12157863.7 mailing date of May 31, 2012.

(Continued)

*Primary Examiner* — Tom Sheng
(74) *Attorney, Agent, or Firm* — Cantor Colburn LLP

(57) ABSTRACT

A measurement device that comprises a display control part that displays a measurement result obtained from a probe that measures a pH or the like, the display control part displays in a switchable manner at least two displaying screens among a numerical value displaying screen that displays the measurement result as a numeric value, an analog displaying screen that displays the measurement result like an analog meter and a graph displaying screen that displays the measurement result as a time series graph, and the display control part switches each of the displaying screens continuously in conjunction with a touch slide operation on the display by moving the displaying screen displayed prior to the touch slide operation to the outside of a displaying area on the display and by moving the other displaying screen to the inside of the displaying area in accordance with the above-mentioned movement.

4 Claims, 19 Drawing Sheets

(56) References Cited

U.S. PATENT DOCUMENTS

| | | |
|---|---|---|
| 2010/0149115 A1 | 6/2010 | Park et al. |
| 2011/0025711 A1* | 2/2011 | Doi .............................. 345/635 |
| 2011/0145705 A1* | 6/2011 | Cheng et al. .................. 715/702 |
| 2011/0167366 A1* | 7/2011 | Wagner ......................... 715/765 |
| 2012/0013562 A1* | 1/2012 | Jyonoshita et al. ........... 345/173 |
| 2012/0019563 A1* | 1/2012 | Misawa et al. ............... 345/661 |
| 2012/0084735 A1* | 4/2012 | Sirpal ........................... 715/863 |

FOREIGN PATENT DOCUMENTS

| | | |
|---|---|---|
| JP | 2009257927 A | 11/2009 |
| JP | 2010009104 A | 1/2010 |
| JP | 2010015239 A | 1/2010 |
| WO | 2008030976 A2 | 3/2008 |
| WO | 2011001001 A1 | 1/2011 |

OTHER PUBLICATIONS

Seungyon Lee et al.: The performance of touch screen soft buttons', Proceedings of the 27th International Conference on Human Factors in Computing Systems, CHI 2009, Jan. 1, 2009, p. 309.

Summary of the Office Action dated Jun. 10, 2014 issued in JP Application No. 2011-047026, with English remarks.

* cited by examiner (a)

(b)

ated in accordance with the above rules.

MEASUREMENT DEVICE

FIELD OF THE ART

This invention relates to a measurement device that is used for various chemical measurements such as a pH, an oxidation-reduction potential, an ionic concentration, electric conductivity or the like.

BACKGROUND ART

Recently, a measurement device not only for measuring a pH or the like but also for meeting user's needs such that various functions are added has been developed. For example, if we focus attention on a function of displaying a measurement result on a display, there is a measurement device that displays the measurement result with a scale and a pointer like an analog meter or a measurement device that displays the measurement result on a time-series graph (Patent document 1). The display can be switched to the other with an operation of pushing an operation button arranged on the lower side of the display by a user.

However, for the measurement device having multiple functions there is a tendency that a number of buttons becomes large as various functions are added. And there is a problem that it becomes difficult for a user to grasp where the operation button he or she wants to operate is so that the operation becomes hard to understand.

Furthermore, especially a user who is inexperienced in operation might have concerns about whether or not the operation is right at a time when the user intends to switch the displaying screen. Since it is not until the displaying screen is verified after the operation to switch is completed that whether or not the operation is right, the user cannot help conducting an operation to switch the displaying screen without eliminating the concern.

PRIOR ART DOCUMENTS

Patent Documents

Patent document 1: Japanese Unexamined Patent Application Publication No. 2004-325077

DISCLOSURE OF THE INVENTION

Problems to be Solved by the Invention

The present claimed invention intends to solve all of the problems and a main object of this invention is to provide a measurement device whose displaying screens can be switched by a user with an intuitive and easily recognizable operation and that the switch operation can be conducted with security even though the user is not familiar with the operation.

Means to Solve the Problems

More specifically, a measurement device in accordance with this invention is a measurement device comprising a display control part that displays a measurement result obtained by a probe that measures at least either one of a pH, an oxidation-reduction potential, an ionic concentration and electric conductivity by making contact with an object to measured on a display, and is characterized by that the display control part displays at least two displaying screens in a switchable manner among a numerical value displaying screen that displays the measurement result as a numerical value, an analog displaying screen that displays a series of a scale on a predetermined position of which a value is assigned and an indication device that indicates a position corresponding to the measurement result on the scale, and a graph displaying screen that displays the measurement result as a time series graph on a coordinate system where one axis indicates a time and the other axis indicates the measurement result, the display is a touch panel type display, and the display control part switches each of the displaying screens continuously in conjunction with a touch slide operation on the display by moving the displaying screen displayed prior to the touch slide operation to the outside of a displaying area on the display and by moving the other displaying screen to the inside of the displaying area in accordance with the above-mentioned movement.

In accordance with the measurement device of the first embodiment, since the display control part can switch the displaying screen in conjunction with the touch slide operation of the touch panel type display, it is possible for the user to switch the displaying screen just by conducting the touch slide operation. Accordingly, since it is not necessary for the user to conduct troublesome operations such as selecting an appropriate button among various buttons to be operated, it is possible for the user to switch the displaying screen intuitively with an easily recognizable operation. In addition, in conjunction with the touch slide operation on the display since the display control part moves the displaying screen that has been displayed prior to the touch slide operation to outside of the displaying area of the display and moves the other displaying screen to inside of the displaying area so that each of the displaying screens is continuously switched, it is possible for the user to verify the displaying screen after switch during a process of switching operation. Accordingly, since it is possible for the user to verify whether the operation is right or not prior to completion of the switching operation, the user can conduct the switching operation without anxiety.

In order to further improve usability for a user, in case that a sliding distance of the touch slide operation is a predetermined value or more, it is preferable that the display control part displays the other displaying screen, and in case that the sliding distance of the touch slide operation is less than the predetermined value, it is preferable that the display control part displays the displaying screen that has been displayed prior to the touch slide operation.

In order to make it easy to understand the switching operation, in case that the touch operation is conducted on the display, it is preferable that the display control part displays a guide indicating a direction to which the displaying screen is movable.

Effect of the Invention

Accordingly, in accordance with this invention, it is possible for the user to switch the displaying screen by the intuitive and easily recognizable operation so that the user can conduct the switch operation with ease by verifying the displaying screen after switch in the middle of the switching operation.

EXPLANATION OF CODES

Figure 1:
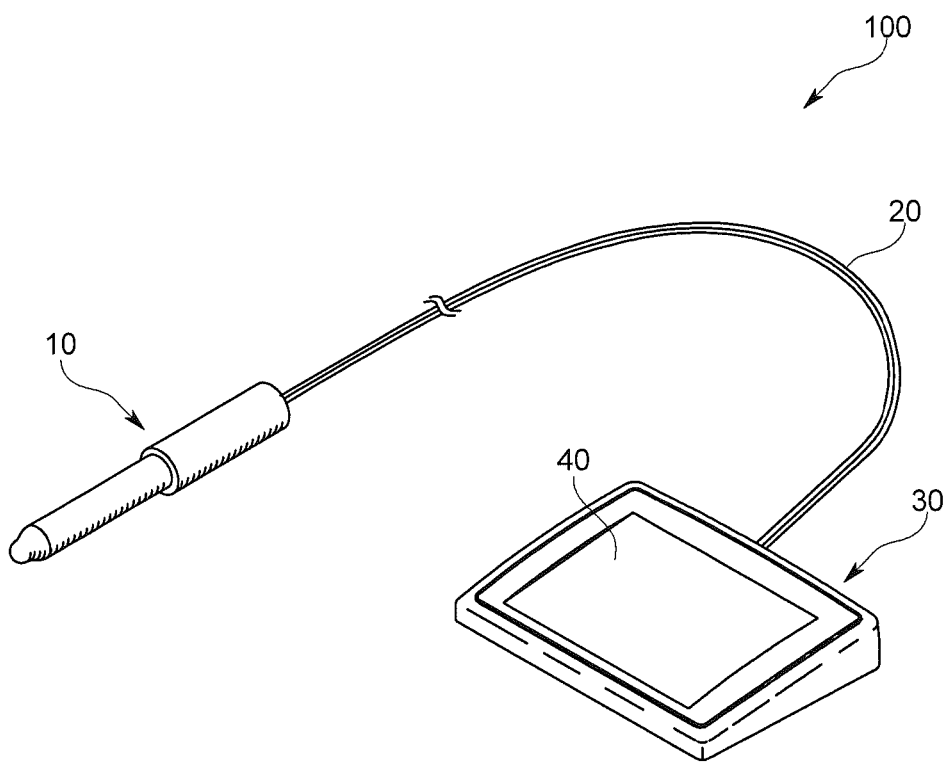
FIG. 1 is a pattern overall view of a measurement device in accordance with a first embodiment of this invention.

100 . . . measurement device
10 . . . probe
33 . . . display control part
40 . . . display (touch panel type display)
50 . . . guide
4 . . . input direction detection part
6 . . . guide display part
W1 . . . graph displaying screen
W2 . . . analog displaying screen
W3 . . . numerical value displaying screen
A1 . . . measurement result displaying area
A2 . . . peripheral area
A3 . . . variable displaying area

BEST MODES OF EMBODYING THE INVENTION

A measurement device 100 in accordance with a first embodiment of this invention will be explained with reference drawings.

The measurement device 100 is a water quality measurement device that measures a pH, an oxidation-reduction potential, an ionic concentration, electric conductivity, a turbidity and a concentration of a contained component such as dissolved oxygen of an object to be measured such as an aqueous solution or food.

Concretely, as shown in FIG. 1, the measurement device 100 comprises a probe 10 as being a measurement part to measure an object to be measured and a body 30 electrically connected to the probe 10 through a cable 20. The probe 10 and the body 30 may be connected through a wireless radio communication. Each part will be explained in detail.

The probe 10 is to measure the object to be measured. The probe 10 is detachable from the body 30, and can be exchanged tailored to a measurement object. As the probe 10 represented are a pH measurement probe, an oxidation-reduction potential measurement probe, an ionic concentration measurement probe, an electric conductivity measurement probe, a dissolved oxygen measurement probe, and turbidity measurement probe. The pH measurement probe will be explained as the probe 10 in this embodiment.

The pH measurement probe 10 comprises a glass electrode and a reference electrode each of which is integrally formed. A detection part of the glass electrode and the reference electrode is arranged at a distal end part of the pH measurement probe 10. The detection part makes contact with the object to be measured, and the pH measurement probe 10 detects a potential difference between the glass electrode and the reference electrode and outputs a detection signal showing the potential difference.

The body 30 is generally in a plate shape and a tablet type computer wherein a display 40 and a control mechanism to control whole of the measurement device 100 are integrally formed.

The display 40 is a touch panel type display and functions as both a display device and an input device. The displaying area that displays an image on the display 40 also functions as an area to receive a position input though a touch operation. In addition, a method for position detection of the touch panel type display 40 is of a single touch type that allows only one point position input simultaneously and of an electrostatic capacity method in this embodiment. The position input is conducted not only by making contact with a finger of a user but also by making close proximity with a finger of a user. Accordingly, a touch operation in this embodiment means an operation that the user makes his or her finger tip or a position input member such as a touch pen to contact with or to come close to the display 40, and corresponds to a click operation for a mouse. In case of the touch operation, the user may separate his or her fingertip from the display 40 just after the contact or close proximity with the finger, or may keep a state that the fingertip contacts or in close proximity to the display 40 for a predetermined period of time. In addition, a touch slide operation means an operation that the user moves his or her fingertip in a state that the fingertip makes contact with or in close proximity to the display 40 after the touch operation, and corresponds to a drag operation for a mouse.

Figure 2:
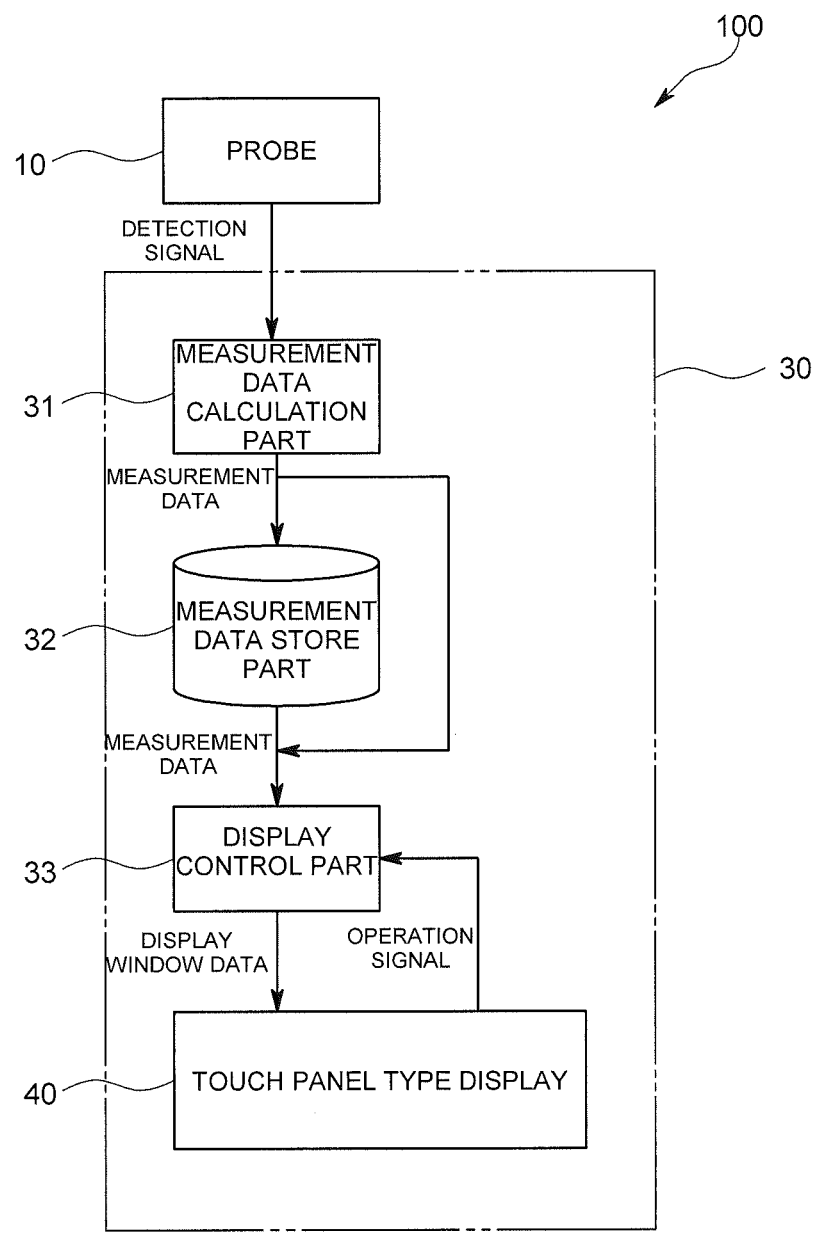
FIG. 2 is a function block view of the measurement device in accordance with the first embodiment.

The control mechanism comprises a CPU, a memory and an A/D converter physically. The control mechanism stores predetermined programs in the memory and produces functions as a measurement data calculation part 31, a measurement data store part 32 and a display control part 33 as shown in FIG. 2 by cooperating with the CPU and its peripheral devices according to the programs.

The measurement data calculation part 31 receives a detection signal from the probe 10 and calculates a measurement data showing a pH measurement value of the object to be measured based on a value of the detection signal and an analytical curve stored in the memory.

The measurement data store part 32 is set in a predetermined area of the memory and successively stores the measurement data calculated by the measurement data calculation part 31 one after another.

The display control part 33 displays the measurement result obtained from the probe 10 on the display 40. The display control part 33 displays plurality of displaying screens W1, W2, and W3 in a switchable manner, and in this embodiment a graph displaying screen W1 (FIG. 3), an analog displaying screen W2 (FIG. 4) and a numerical value displaying screen W3 (FIG. 5) are displayed in a switchable manner.

Figure 3:
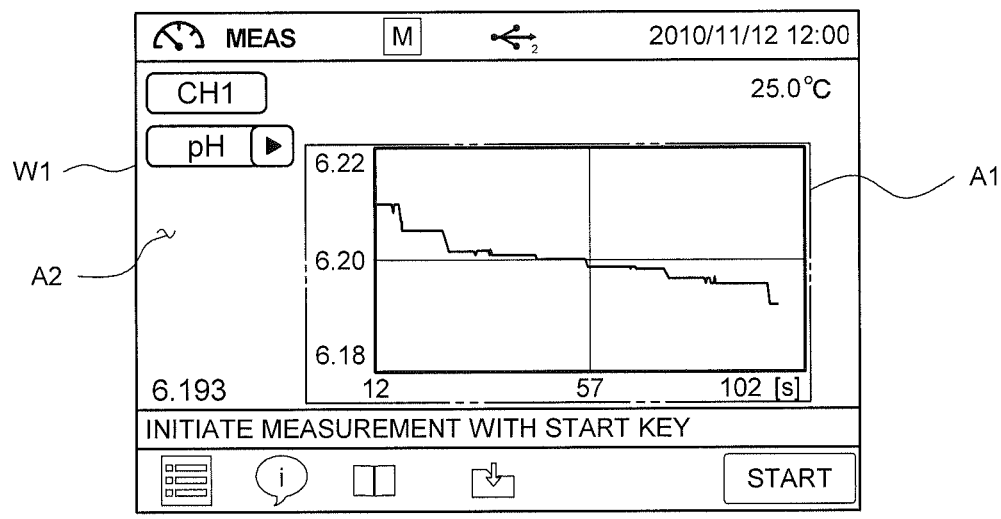
FIG. 3 is a screen configuration diagram showing an example of a graph displaying screen in accordance with the first embodiment.

Each of the displaying screens W1, W2 and W3 will be explained. As shown in FIG. 3, the graph displaying screen W1 displays the measurement result as a time-series graph on a coordinate system where a time axis indicating a time is expressed on a horizontal axis and a measurement axis indicating a pH measurement result is expressed on a vertical axis. Ordinarily, a value assigned on the time axis and a value assigned on the measurement axis are automatically set so as to be appropriate in accordance with the measurement result. In this embodiment, a numerical value range of the time axis is set so as to be a predetermined width and to include the latest measurement time, and the numerical value range of the measurement axis is set so as to include the maximum value and the minimum value of the pH indicated by the measurement result. A middle value of the measurement axis is set so as to be a numerical value made to the second decimal place. For example, in case that a mean value of the maximum value and the minimum value of the pH is calculated as 6.207 as being a value made to the third decimal place, 6.20 as being a value made to the second decimal place that is the closest to 6.207 is set as the middle value.

Figure 4:
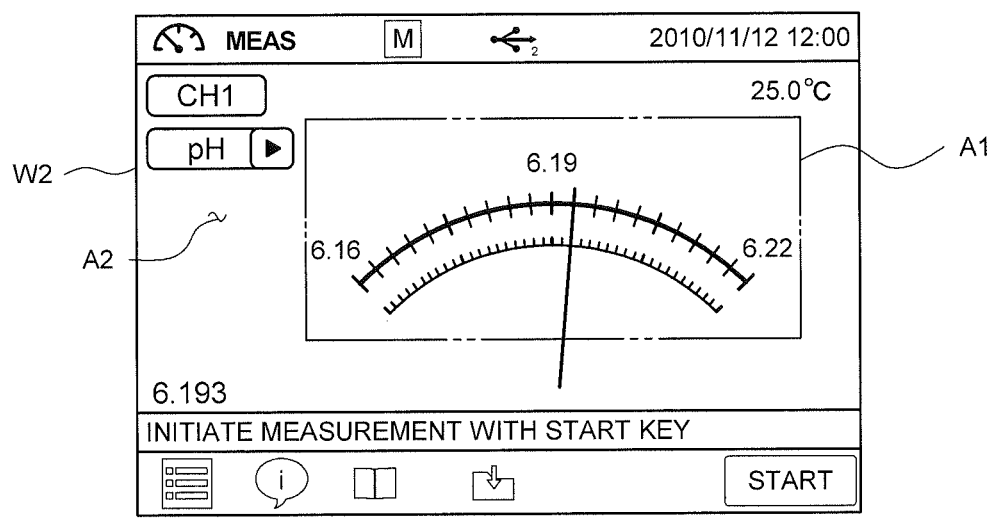
FIG. 4 is a screen configuration diagram showing an example of an analog displaying screen in accordance with the first embodiment.

As shown in FIG. 4, the analog displaying screen W2 displays a series of a scale on a predetermined position of which a value is assigned and an indication device that indicates a position on the scale corresponding to the latest pH measurement result. In this embodiment, the scale is arranged radially equally spaced apart and a pointer rotates on the scale. Ordinarily, the value assigned on the scale is so arranged to be automatically set appropriately in accordance with the measurement result. In this embodiment, an upper limit value, a lower limit value and a middle value as being a mean value of the upper limit value and the lower limit value are assigned on the scale. The middle value is determined tailored to the pH measurement value, and the upper limit value and the lower limit value are set so as to make an interval between each value at a predetermined value (0.03 in this embodiment). For example, in case that the pH measurement value is 6.193, 6.19 as being a value that is the closest to the 6.193 and that is made to the second decimal point is set as the middle value. Furthermore, 6.16 and the 6.22 are set as the lower limit value and the upper limit value.

Figure 5:
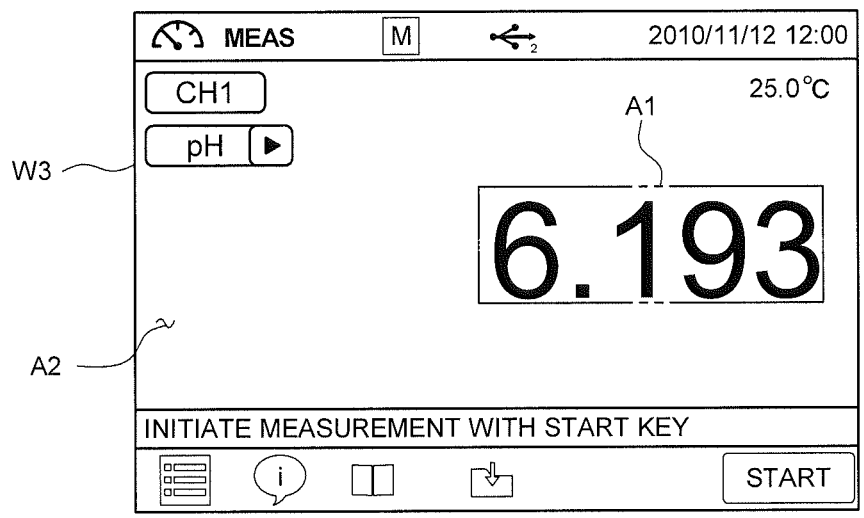
FIG. 5 is a screen configuration diagram showing an example of a numerical value displaying screen in accordance with the first embodiment.

As shown in FIG. 5, the numerical value displaying screen W3 displays the latest pH measurement result as a numerical value, and in this embodiment displayed is a value made to the third decimal point.

Then in this embodiment, when a user conducts a touch slide operation on the display 40, the display content of the measurement result is changed in accordance with the touch slide operation. Concretely, the display control part 33 switches the displaying screen W1, W2, W3 in conjunction with the touch slide operation.

Figure 6:
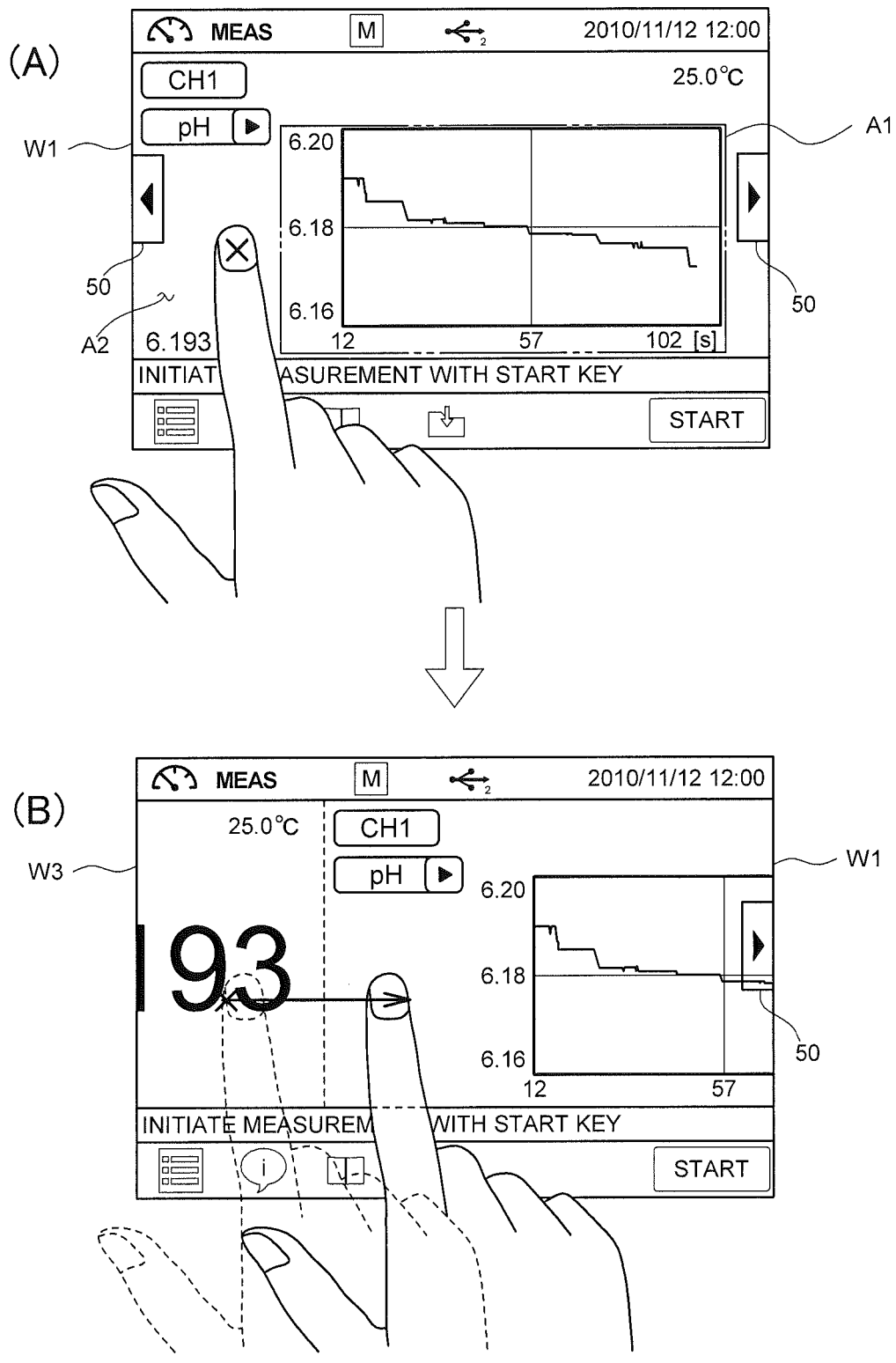
FIG. 6 is a screen configuration diagram showing a process of switching the graph displaying screen to the numerical value displaying screen in accordance with the first embodiment.

First, a case that the display control part 33 switches the displaying screen W1, W2, W3 will be explained with reference to FIG. 6 through FIG. 8. FIG. 6 (A) shows an example that the displaying screen prior to switch is the graph displaying screen W1.

Plurality of areas are set on each of the displaying screens W1, W2 and W3 starting with the graph displaying screen W1. Concretely, a first displaying area A1 (hereinafter also called as a measurement result displaying area) that is formed on a center part of each displaying screen W1, W2, W3 and that displays the measurement result, and a second displaying area A2 (hereinafter also called as a peripheral area) that is formed on the periphery of each displaying screen W1, W2, W3 and that is different from the first displaying area A1 are set. In this embodiment, a changed mode of the display content in case that the touch slide operation is conducted on the measurement result displaying area A1 is different from a changed mode of the display content in case that the touch slide operation is conducted on the peripheral area A2. In case that the touch slide operation is conducted on the peripheral area A2, the display control part 33 switches the displaying screen W1, W2, W3. The touch slide operation conducted on the peripheral area A2 by the user means that an area where the user first touches at a time of the touch slide operation is the peripheral area A2. In addition, a case that the touch slide operation is conducted on the measurement result displaying area A1 will be described later.

When the user conducts the touch slide operation in the right direction on the peripheral area A2 of the graph displaying screen W1, the display control part 33 switches the graph displaying screen W1 to the numerical value displaying screen W3. More specifically, when the user conducts the touch slide operation, the display control part 33 receives an operation signal indicating the touch slide operation from the display 40. The display control part 33 moves the displaying screen (the graph displaying screen W1, in this embodiment) that has been displayed prior to the touch slide operation to outside of the displaying area of the display 40 and moves the adjacent another displaying screen (the numerical value displaying screen W3, in this embodiment) to inside of the displaying area in conformity to the movement of the graph displaying screen W1 in conjunction with the touch slide operation. With this movement, each of the displaying screen W1, W3 is continuously switched.

As shown in FIG. 6 (B), an end part of the displaying screen W1 prior to switch is continuously connected to an end part of the displaying screen W3 after switch. Accordingly, a distance (an area) that the display control part 33 scrolls the displaying screen W1 prior to switch becomes equal to a distance (an area) that the display control part 33 scrolls the displaying screen W3 after switch. In addition, a slide distance of the touch slide operation is so set to be equal to a distance that the displaying screen W1, W3 moves. The slide distance means a distance from a position where the user contacts his or her finger with the display 40 or places the finger close to the display 40 to a position where the user separates the finger from the display 40 after the user moves the finger while keeping the state that the finger is contact or in close proximity to the display 40.

When the slide distance of the touch slide operation is a predetermined value or over at a time when the touch slide operation is completed, the display control part 33 displays the displaying screen (the numerical value displaying screen W3, in this embodiment) after switch. When the slide distance is less than the predetermined value, the display control part 33 displays the displaying screen (the graph displaying screen W1, in this embodiment) prior to switch. Concretely, at a time when the touch slide operation is competed, if more than or equal to a half of the displaying screen W3 after switch is displayed, it is so set that the screen W3 after switch is displayed, otherwise it is so set that the displaying screen W1 prior to switch is displayed.

As shown in FIG. 6 (B), if an area of the displaying screen (the numerical value displaying screen W3) after switch in the displaying area of the display 40 is compared with an area of the displaying screen (the graph displaying screen W1) prior to switch in the displaying area of the display 40, the area of the displaying screen W1 prior to switch becomes larger than that of the displaying screen W3 after switch. In this state, if the user terminates the touch slide operation, the display control part 33 moves each of the displaying screens W1, W3 in a direction opposite to a direction that the touch slide operation is conducted on the display 40 and returns to the graph displaying screen W1. In other words, the display control part 33 moves the graph displaying screen W1 so as to coincide the both end parts of the graph displaying screen W1 with the both end parts of the displaying area of the display 40. Meanwhile, in case that the area of the numerical value displaying screen W3 is larger, the display control part 33 switches the graph displaying screen W1 to the numerical value displaying screen W3.

At a time when the user touches the peripheral area A2, the display control part 33 displays a guide 50 indicating a direction that can be operated with the touch slide operation. in this embodiment, the display control part 33 displays arrows indicating right and left (FIG. 6 (*a*)). Consecutively, as shown in FIG. 6 (B), when the user initiates the touch slide operation in the right direction, the display control part 33 displays only the guide 50 indicating the right direction and eliminates the other guide 50 and informs the user of the received input operation.

Figure 7:
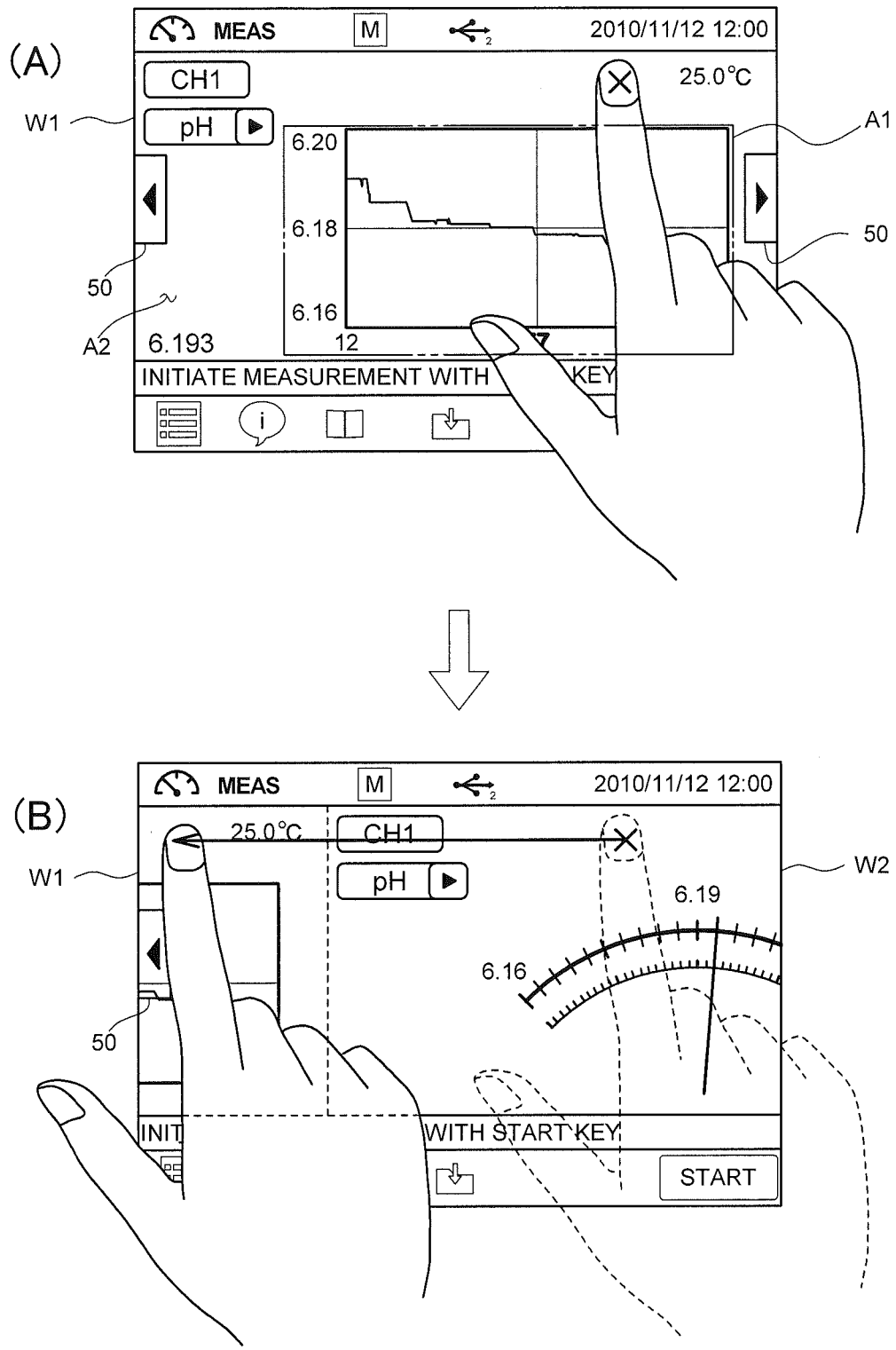
FIG. 7 is a screen configuration diagram showing a process of switching the graph displaying screen to the analog displaying screen in accordance with the first embodiment.
Figure 8:
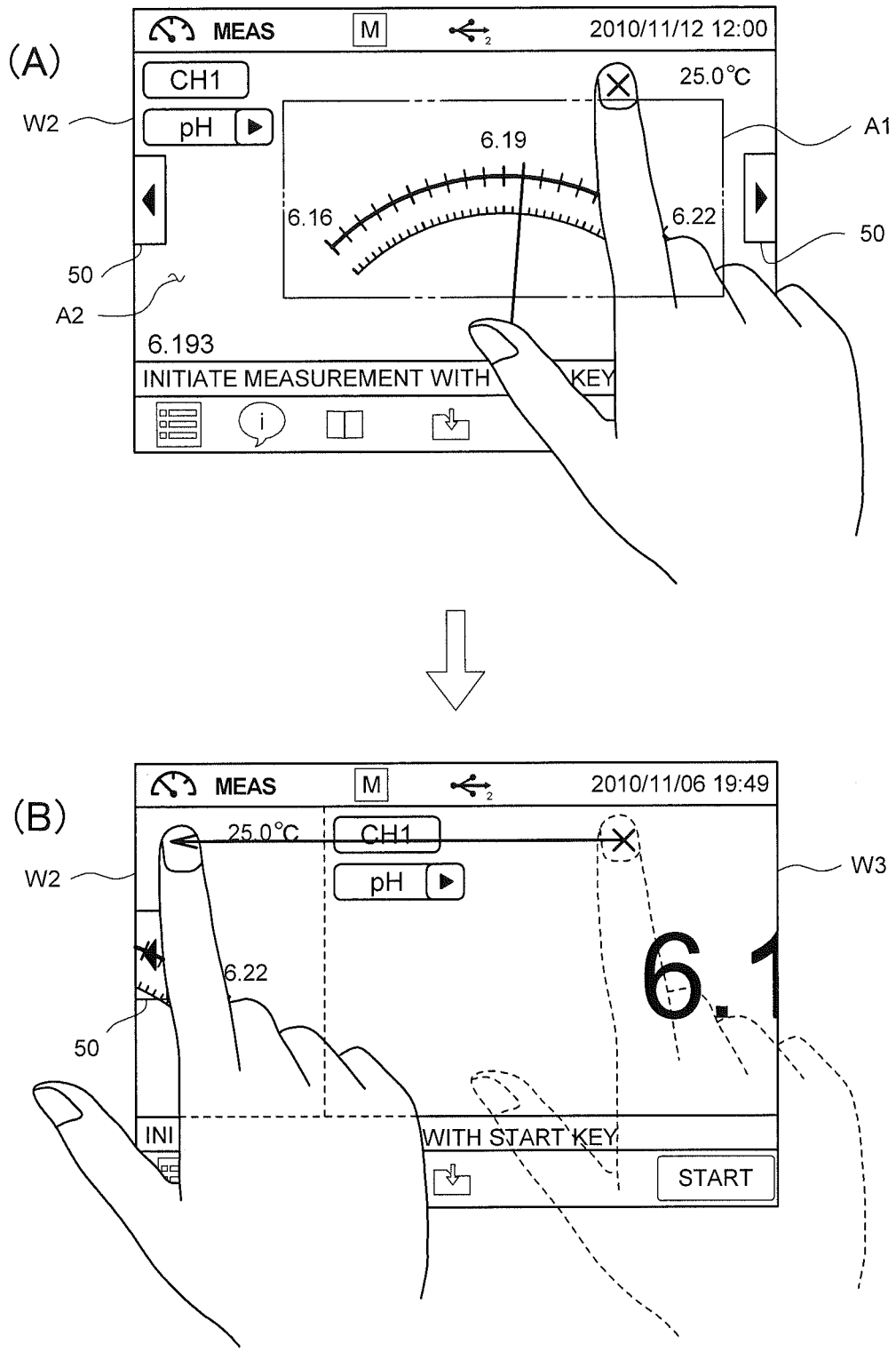
FIG. 8 is a screen configuration diagram showing a process of switching the analog displaying screen to the numerical value displaying screen in accordance with the first embodiment.

Similarly, when the user conducts the touch slide operation in the left direction on the peripheral area A2 of the graph displaying screen W1, the display control part 33 switches the graph displaying screen W1 to the analog displaying screen W2 (FIG. 7 (A) to FIG. 7 (B)).

The displaying screen prior to switch may be the analog displaying screen W2 or the numerical value displaying screen W3. For example, as shown in FIG. 8, when the user conducts the touch slide operation in the left direction on the peripheral area A2 of the analog displaying screen W2, the display control part 33 switches the analog displaying screen W2 to the numerical value displaying screen W3 (FIG. 8 (A) to FIG. 8 (B)). In addition, for the graph displaying screen W1 and the analog displaying screen W2, in case that the touch slide operation is conducted on the peripheral area A2, the displaying screen W1, W2 is switched to another screen. Contrarily, for the numerical value displaying screen W3, in case that the touch slide operation is conducted also on the measurement result displaying area A1 in addition to the peripheral area A2, the displaying screen W3 is switched to another screen.

Figure 9:
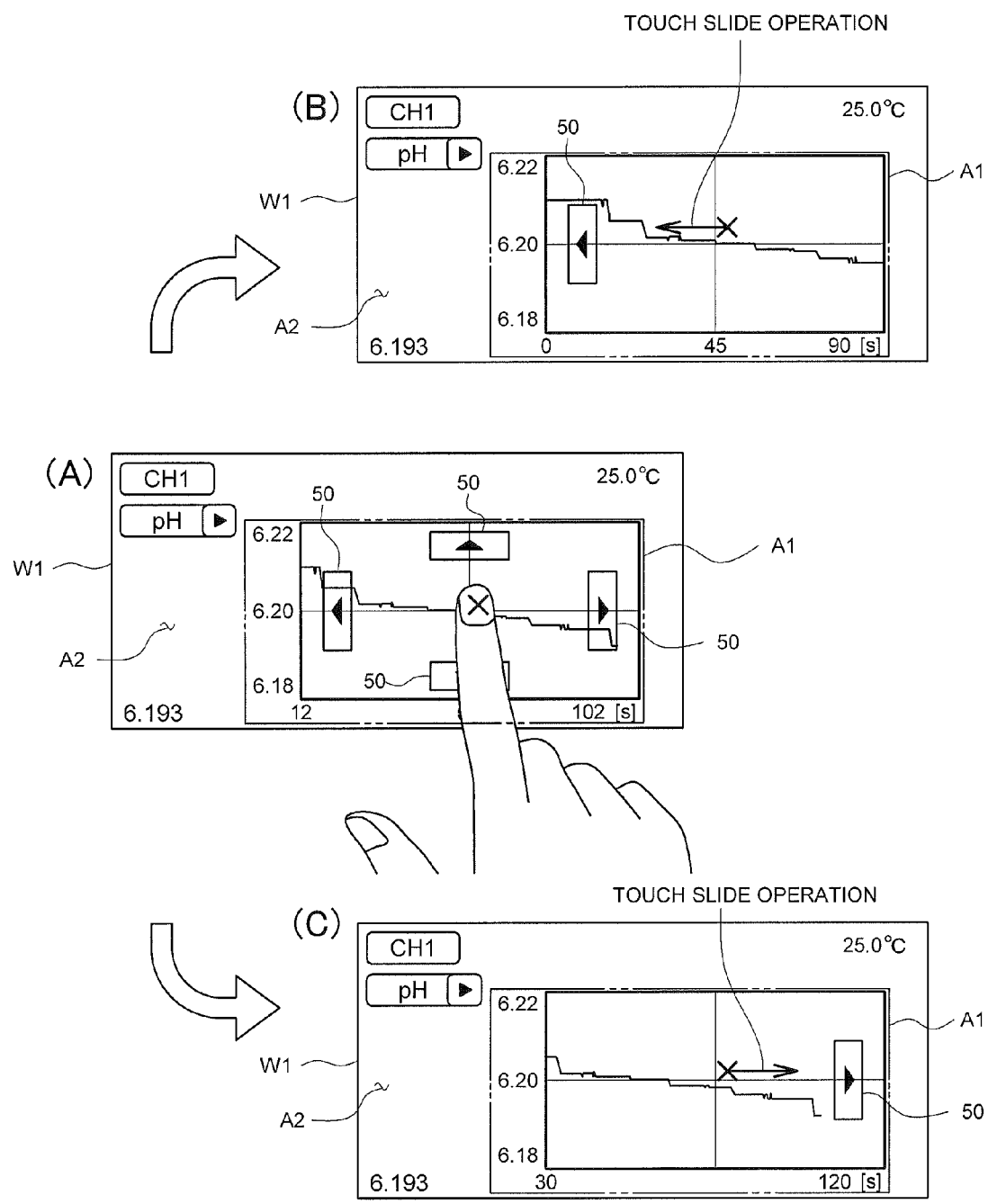
FIG. 9 is a screen configuration diagram showing a process of changing a numerical value range of a time axis in the graph displaying screen in accordance with the first embodiment.

In addition, the display control part 33 of this embodiment changes a numerical value range of a coordinate axis or a numerical value range indicated by the scale in accordance with the touch slide operation. A case that the display control part 33 changes the numerical value range of the coordinate axis of the graph displaying screen W1 will be explained with reference to FIG. 9 and FIG. 10. In this embodiment, a change mode of the display content in case that the touch slide operation is in a first direction (a time axis in this embodiment) is so arranged to be different from a change mode of the display content in case that the touch slide operation is in a second direction (a measurement axis in this embodiment) that is different from that of the first direction. First, a case that the user conducts the touch slide operation in the time axis will be explained. FIG. 9 (A) shows an example wherein the numerical value range of the time axis of the graph displaying screen W1 prior to the touch slide operation falls within a range between 12 second and 102 second.

When the user conducts a touch slide operation on the measurement result displaying area A1 of the graph displaying screen W1 to the left direction along the time axis, the display control part 33 moves the numerical value range of the time axis. More specifically, when the user initiates the touch slide operation, the display control part 33 receives an operation signal indicating the touch slide operation from the display 40. Then, an automatic setting to the numerical value range of the time axis is released and switched to a manual setting.

In conjunction with the above-mentioned touch slide operation, the display control part 33 moves the numerical value range of the time axis by decreasing the upper limit value and the lower limit value while keeping a difference between the upper limit value and the lower limit value of the numerical value range of the time axis. FIG. 9 (B) shows an example wherein the numerical value range of the time axis of the time series graph moves from 0 second to 90 second. In addition, in conjunction with the above-mentioned touch slide operation, the display control part 33 moves the time series graph corresponding to the moved numerical value range inside of the displaying area of the display 40. As a result of this, the displaying range of the time series graph continuously moves and the past time series graph in the numerical value range of the time axis after change is displayed.

After the user terminates the touch slide operation, the numerical value range of the time axis is kept in a state after automatically set until the next touch operation. At a time when the user separates his or her finger without substantially moving the finger from the position where the finger contacts or is in close proximity after the user conducts the touch operation, the numerical value range of the time axis returns to the automatic set state and the latest time series graph is displayed. Meanwhile, at a time when the user moves the finger in a state the finger contacts or is in close proximity after the user conducts the touch operation, the display control part 33 further changes the numerical value range of the time axis.

In case that the user wants to display a time series graph corresponding to the numerical value range later than the numerical value range of the time axis that is presently displayed, the user conducts the touch slide operation in the right direction along the time axis. FIG. 9 (C) shows an example that the numerical value range of the time axis moves to a range from 30 second to 120 second.

Figure 10:
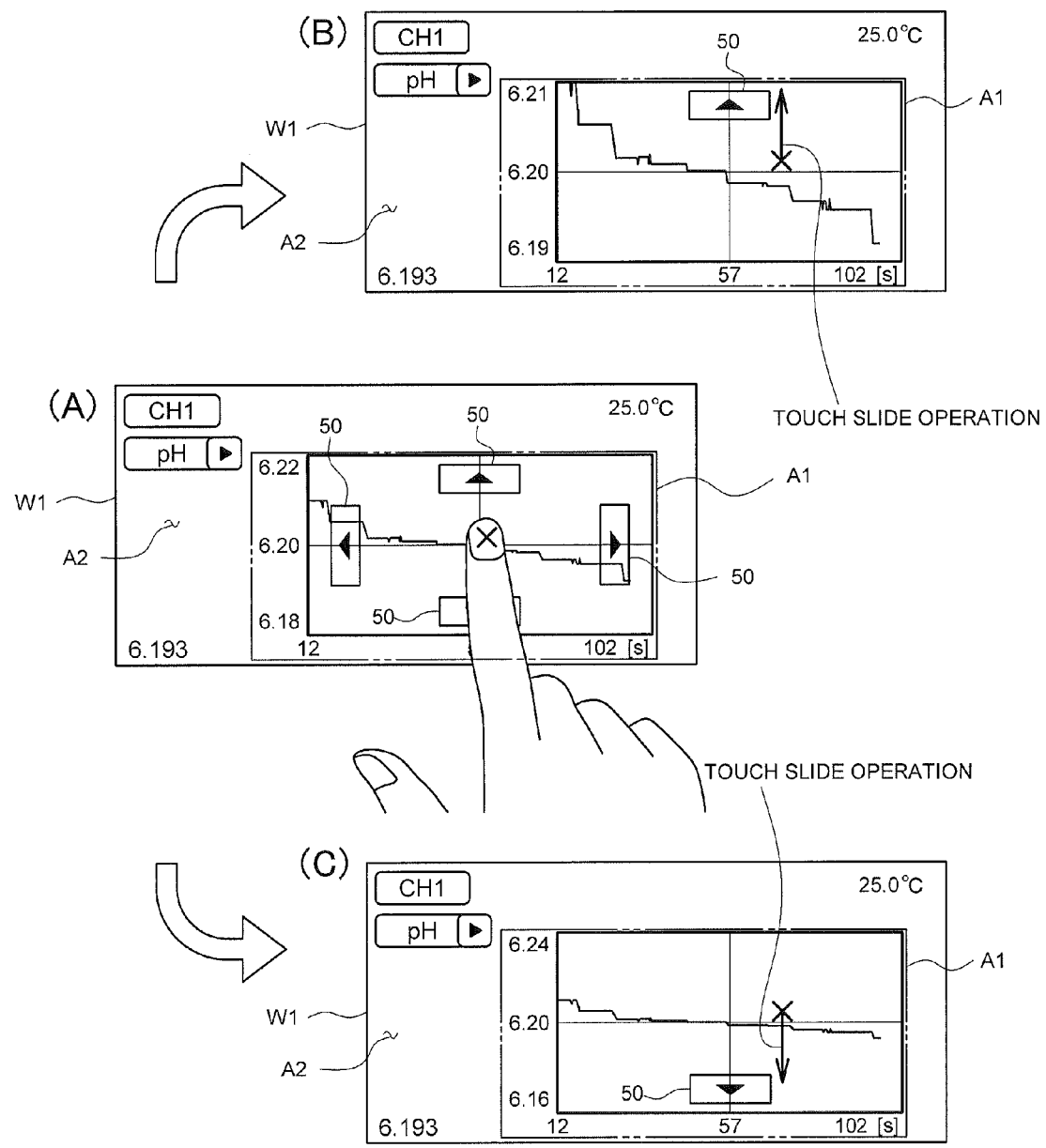
FIG. 10 is a screen configuration diagram showing a process of changing a numerical value range of a measurement axis in the graph displaying screen in accordance with the first embodiment.

A case that the display control part 33 enlarges or reduces the numerical value range of the measurement axis of the graph displaying screen W1 by conducting the touch slide operation in the measurement axis by the user will be explained with reference to FIG. 10. FIG. 10 (A) shows an example wherein the numerical value range of the measurement axis of the graph displaying screen W1 is a range between 6.18 and 6.22 prior to the touch slide operation.

As shown in FIG. 10 (B), when the user conducts the touch slide operation upward along the time axis on the measurement result displaying area A1 of the graph displaying screen W1, the display control part 33 reduces the numerical value range of the measurement axis. More specifically, the display control part 33 decreases a difference between the middle value and the lower limit value and a difference between the middle value and the upper limit value by the same amount while keeping the middle value (6.20 in this embodiment) as a mean value of the upper limit value and the lower limit value of the numerical value range of the measurement axis. FIG. 10 (B) shows an example that the numerical value range of the measurement axis after change becomes a range between 6.19 and 6.21. The display control part 33 displays the time series graph corresponding to the numerical value range of the measurement axis after change.

Similarly, when the user conducts the touch slide operation downward along the time axis, the display control part 33 enlarges the numerical value range of the measurement axis. FIG. 10 (C) shows an example that the numerical value range of the measurement axis after change becomes a range between 6.16 and 6.24.

At a time when the user conducts the touch operation on the display 40, the display control part 33 displays a guide 50 indicating a direction to which the touch slide operation can be conducted as shown in FIG. 9 (A). In this embodiment, the display control part 33 displays arrows each of which indicates left, right, top and bottom respectively. Subsequently, at a time when the user initiates the touch slide operation in the left direction along the time axis, the display control part 33 displays only the guide 50 indicating the left direction and erases other guides 50 as shown in FIG. 9 (B) so as to inform the user of the received input operation.

Figure 11:
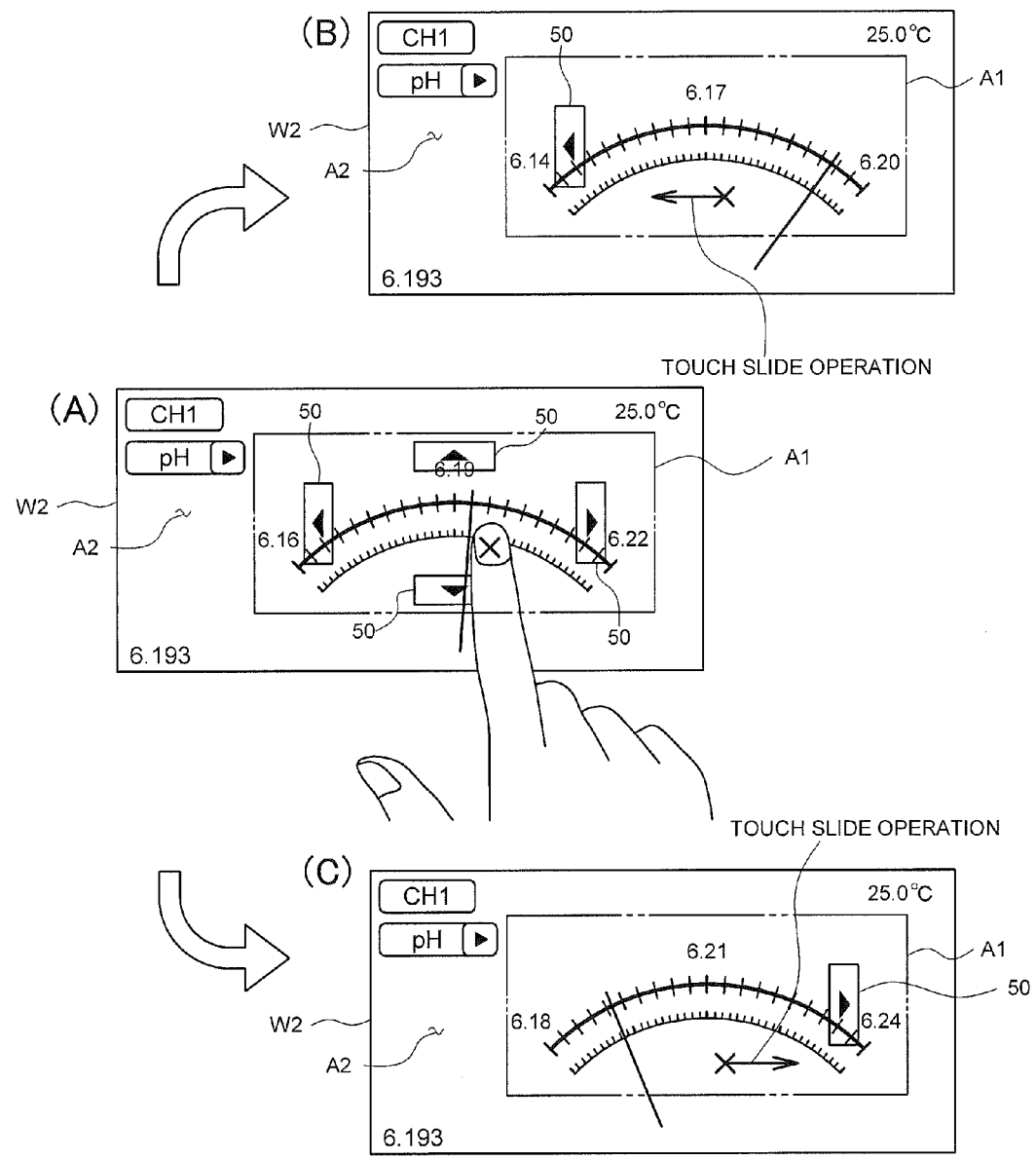
FIG. 11 is a screen configuration diagram showing a process of moving the numerical value range indicated by a scale in the analog displaying screen in accordance with the first embodiment.

A case that the display control part 33 changes the numerical value range indicated by the scale of the analog displaying screen W2 will be explained with reference to FIG. 11 and FIG. 12. First, a case that the display control part 33 moves the numerical value range of the scale will be explained with reference to FIG. 11. FIG. 11 (A) shows an example that the numerical value range indicated by the scale of the analog displaying screen W2 is a range between 6.16 and 6.22 prior to the touch slide operation.

The user conducts the touch slide operation in a direction (the left direction, in this embodiment) that is along an arranged direction of the scale and that is headed from the upper limit value to the lower limit value on the measurement result displaying area A1 of the analog displaying screen W2. Then, the display control part 33 decreases the upper limit value and the lower limit value of the numerical value range indicated by the scale by the same amount. As a result of this, the numerical value range moves while keeping the difference between the upper limit value and the lower limit value. FIG. 11 (B) shows an example that the numerical value range of the scale is changed to a range between 6.14 and 6.20.

In addition, in case that the user wants to move the numerical value range of the scale in the opposite direction, the user may conduct the touch slide operation in a direction (the right direction, in this embodiment) that is along the arranged direction of the scale and that is headed from the lower limit value to the upper limit value. FIG. 11 (C) shows an example that the numerical value range of the scale becomes a range between 6.18 and 6.24.

A case that the display control part 33 reduces or enlarges the numerical value range of the scale will be explained with reference to FIG. 12. FIG. 12 (A) shows an example that the numerical value range prior to the touch slide operation indicated by the scale of the analog displaying screen W2 is a range between 6.16 and 6.22.

Figure 12:
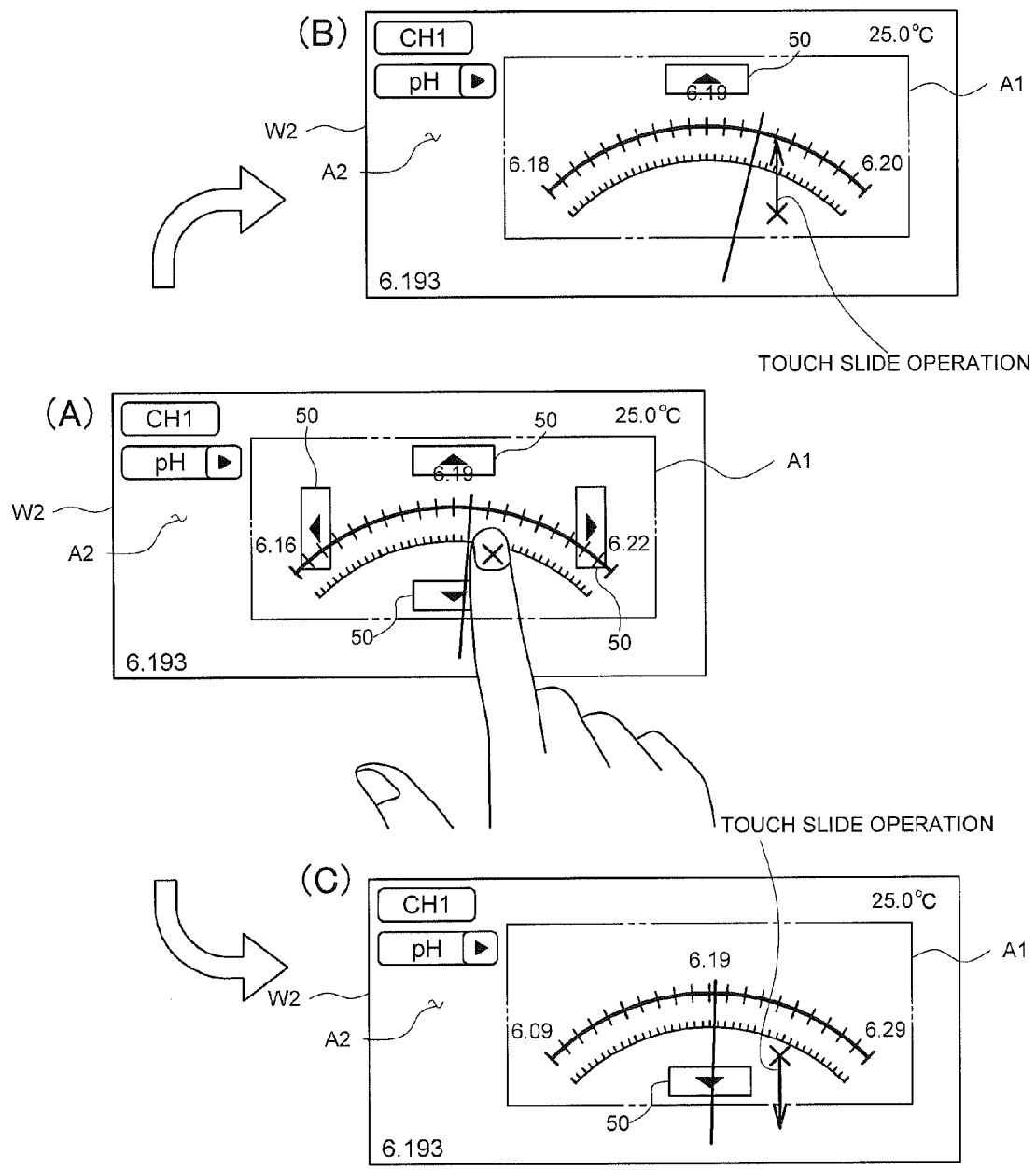
FIG. 12 is a screen configuration diagram showing a process of enlarging and reducing the numerical value range indicated by the scale in the analog displaying screen in accordance with the first embodiment.

At a time when the user conducts the touch slide operation in the upward direction as one of the directions generally orthogonal to the arranged direction of the scale on the measurement result displaying area A1 of the analog displaying screen W2, the display control part 33 reduces the numerical value range of the measurement axis (FIG. 12 (B)). More specifically, the display control part 33 decreases the difference between the middle value and the lower limit value and the difference between the middle value and the upper limit value by the same amount while keeping the middle value (6.19) of the numerical value range indicated by the scale. As a result of this, FIG. 12 (B) shows an example that the numerical value range of the scale after change is a range between 6.18 and 6.20.

Similarly, when the user conducts the touch slide operation downward, the display control part 33 enlarges the numerical value range of the scale. FIG. 12 (C) shows an example that the numerical value range of the scale after change is a range between 6.09 and 6.29.

The guide 50 is also displayed on the analog displaying screen W2, however, since it is the same as that of the graph displaying screen W1, the same numerical codes are given and an explanation thereof will be omitted.

In accordance with the measurement device 100 of the first embodiment, since the display control part 33 can switch the displaying screen in conjunction with the touch slide operation on the touch panel type display 40, it is possible for the user to switch the displaying screen just by conducting the touch slide operation. Accordingly, since it is not necessary for the user to conduct troublesome operations such as selecting an appropriate button among various buttons to be operated, it is possible for the user to switch the displaying screen intuitively with an easily recognizable operation. In addition, in conjunction with the touch slide operation since the display control part 33 initiates scrolling and eliminating the displaying screen prior to switch and initiates scrolling and displaying the displaying screen after switch so that the displaying screen is continuously switched, it is possible for the user to verify the displaying screen after switch during a process of switching operation. Accordingly, since it is possible for the user to verify whether the operation is right or not prior to completion of the switching operation, the user can conduct the switching operation without anxiety.

Furthermore, since the display control part 33 displays the guide 50 indicating the direction to which the touch slide operation can be conducted at a time when the user conducts the touch operation on the display 40, it is possible for the user to intuitively understand the direction to be operated with the touch slide operation without checking with a manual of the measurement device 100 or the like. Furthermore, at a time when the user initiates the touch slide operation, since the display control part 33 displays only the guide 50 corresponding to the received touch slide operation, the user can verify the operation received by the measurement device 100 and conduct the operation without anxiety.

The present claimed invention is not limited to the above-mentioned embodiment. For example, the displaying screen is not limited to the above-mentioned arrangement, in addition to each displaying screen, a menu screen to conduct each setting regarding the measurement device or an explanatory screen that displays an operating instruction may be displayed in a switchable manner.

In addition, the directions to which the touch slide operation can be conducted are left, right, top and bottom in the above-mentioned embodiment, however, the direction may be other directions. For example, the direction may be set in an oblique direction.

Furthermore, at a time when the touch slide operation is conducted on the display, the display control part may enlarge or reduce the numerical value range of the time axis, or the numerical value range of the measurement axis may move while keeping the difference between the upper limit value and the lower limit value.

The slide distance of the touch slide operation is set to be equal to the distance that the displaying screen moves, however, the slide distance may be proportional to the distance that the displaying screen moves. In addition, a relational expression indicating a relation between the slide distance of the touch slide operation and the distance that the displaying screen moves may be previously calculated and the distance that the displaying screen moves may be calculated based on the relational expression. More concretely, it can be represented that the one wherein the more the slide distance of the touch slide operation increases, the more the moving distance increases. The same is applied also to a relationship between the slide distance of the touch slide operation and the changed amount of the numerical value range.

In addition, the measurement result displaying area and the peripheral area are separated on the graph displaying screen and the analog displaying screen in the first embodiment, however they may not be separated. Concretely, even though a case that either of the measurement result displaying area and the peripheral area is operated with the touch slide operation, if the touch slide operation is in the right and left directions, the display control part switches the displaying screen. Furthermore, if the touch slide operation is in the top and bottom directions, the display control part may change the numerical value range of the coordinate axis or the numerical value range indicated by the scale.

Figure 13:
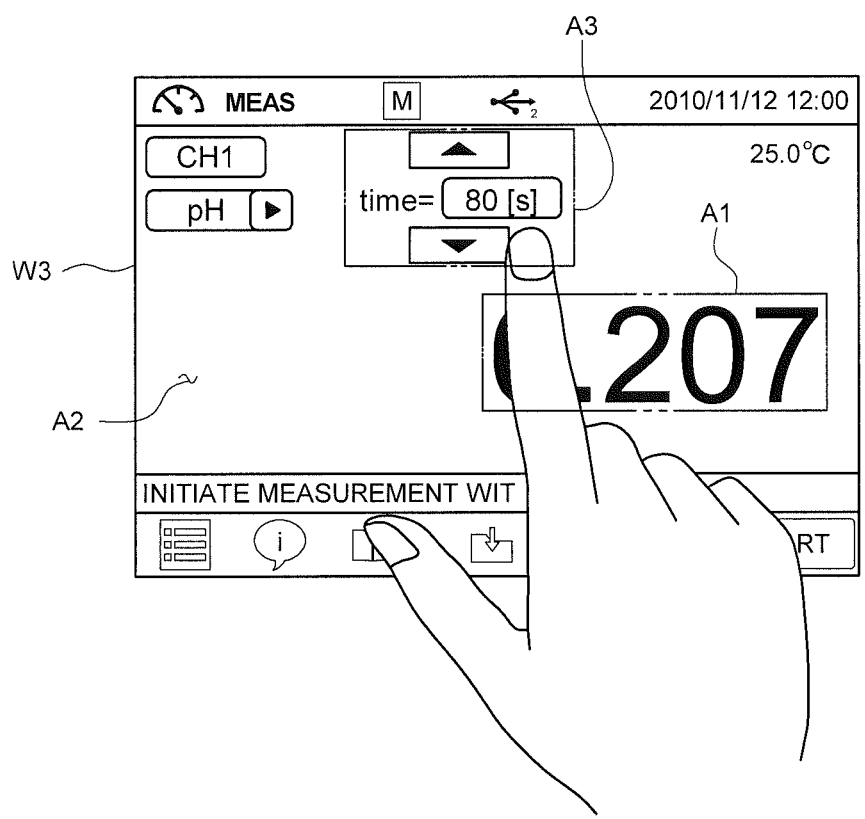
FIG. 13 is a screen configuration diagram showing a state that a variable displaying area is touched in the numerical value displaying screen in accordance with other embodiment.

Furthermore, as shown in FIG. 13, in case the numerical value displaying screen is displayed, if the user selects a measurement time by the touch slide operation, the display control part may display the measurement result corresponding to the selected measurement time. Concretely, a variable displaying area A3 where a variable such as a measurement time is displayed is formed on the numerical value displaying screen. The user may change the measurement time by conducting the touch slide operation on the variable displaying area A3 in the top and bottom direction. Similarly, the display control part may display the measurement result corresponding to the variable on the graph displaying screen or the analog displaying screen.

If we focus attention on the displaying area, an area combined with the area surrounded by the coordinate axis and the area where the value assigned on the coordinate axis is displayed is set as the measurement result displaying area in this embodiment, however, only the area surrounded by the coordinate axis may be set as the measurement result displaying area. The same is applied also to the analog displaying screen.

If we focus attention on the guide, if the user conducts the touch operation on the measurement result displaying area, only the guide of the measurement result displaying area is displayed in this embodiment. The displaying mode of the guide is not limited to this. For example, at a time when the user conducts the touch operation on the measurement result displaying area, the display control part displays the guide of the measurement result displaying area and the guide of the peripheral area. Furthermore, the displaying mode of the guide may vary for each displaying area such that the display control part displays the guide of the measurement result displaying area deep in color and the guide of the peripheral area pale in color. With this arrangement, it is possible for the user to grasp the display content that can be changed by the touch slide operation at once.

In addition, at a time when the user initiates the touch slide operation, the display control part displays only the guide corresponding to the operating direction received by the display control part and erases the other guides. However, even though the user conducts the touch slide operation, the display control part may continue displaying all of the guides indicating the direction to which the touch slide operation can be conducted.

Furthermore, in case that the upper limit value or the lower limit value of the numerical value range reaches a boundary value of a range that can be set due to change of the numerical value range or the like, the display control part may erase the corresponding guide. The numerical value range that can be set is a numerical value range from 0 to 14, for example, in case of the pH. In case of the time, the range is a numerical value range from 0 second to the final measurement time (or from the final measurement time to a time when a predetermined period of time passes).

Figure 14:
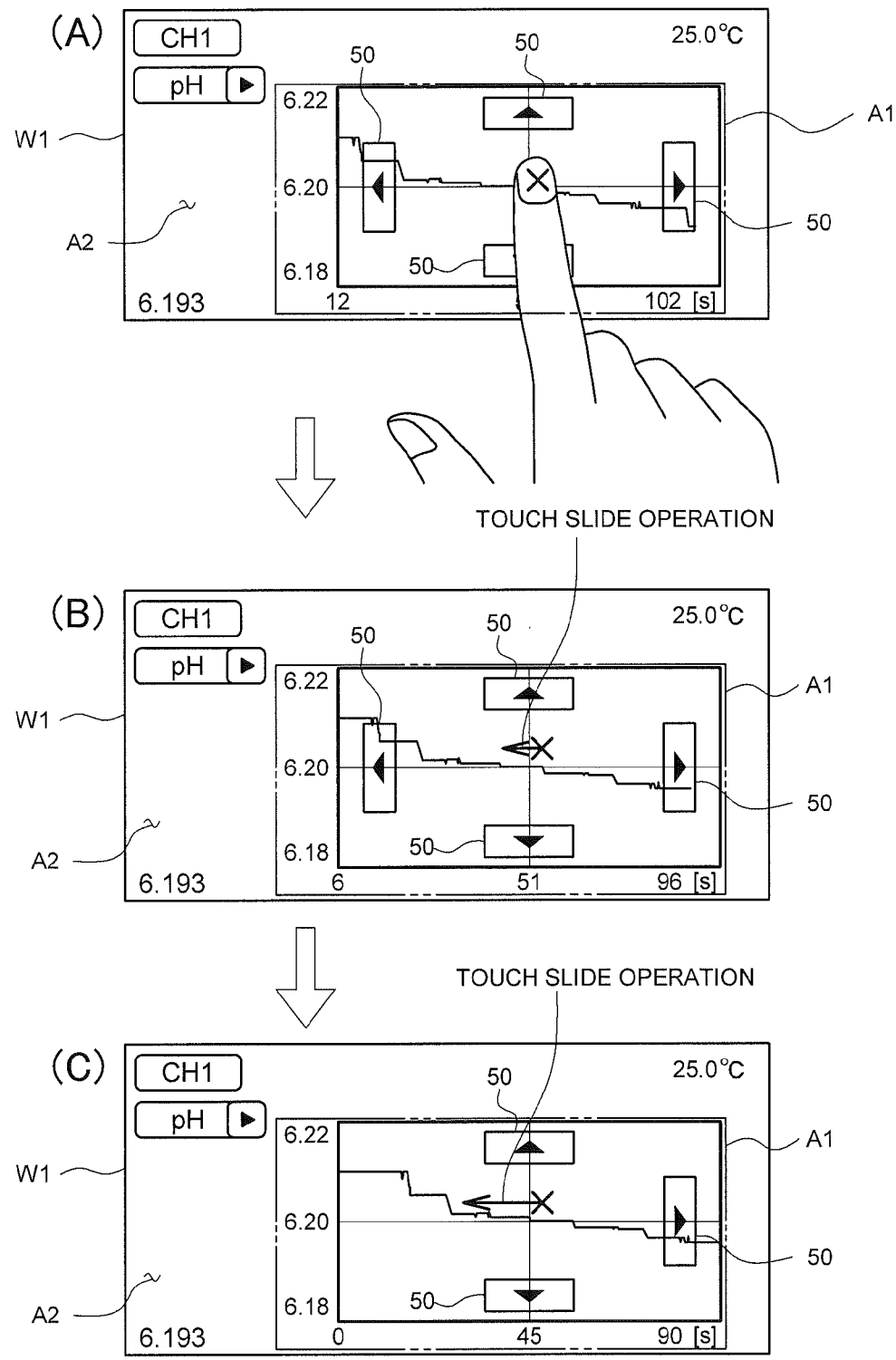
FIG. 14 is a screen configuration diagram showing a process of changing the numerical value range of the time axis in the graph displaying screen in accordance with the other embodiment.

A concrete explanation will be provided. FIG. 14 shows an example of a case that the user conducts the touch slide operation along the time axis. The user conducts the touch slide operation in the left direction along the time axis so that the past time series graph is displayed (FIG. 14 (A) to FIG. 14 (B)). At a time when the lower limit value of the numerical value range of the time axis reaches 0 second, there exists no measurement data obtained in the past (FIG. (C)). Accordingly, the display control part erases the guide indicating the left direction and informs the user that the numerical value range of the time axis cannot be moved further in the left direction. The same is also applied to a case that the numerical value range of the time axis is enlarged or reduced or a case that the numerical value range of the measurement axis or the numerical value range of the scale is changed. In accordance with this arrangement, it is possible for the user to intuitively understand the direction to which the display content cannot be changed even though the user inputs the touch slide operation.

Furthermore, the display control part displays the arrow as the guide in the above-mentioned embodiment, however, it may display a text indicating a display content that can be changed or a reduced screen such as a thumbnail of the displaying screen after switch.

In this embodiment, in case of enlarging or reducing the numerical value range of the measurement axis, the middle value of the measurement axis prior to change is set as a middle value of the measurement axis after change. However, it is not limited to this. For example, in case that the user conducts the touch operation, the measurement value indicated by the position where the user first touches may be set as the middle value of the measurement axis after change. Concretely, in case that the user first conducts the touch operation on the position indicating 6.207 and then conducts the touch slide operation along the measurement axis, 6.207 is set as the middle value of the measurement axis after change.

In addition, in case that the user conducts the touch slide operation, the measurement value at a time indicated by the position where the user first conducts the touch operation may be set as the middle value of the measurement axis after change. Concretely, in case that the user first conducts the touch operation on the position indicating 60 second and then conducts the touch slide operation along the measurement axis, the measurement value at a time of 60 second is set as the middle value of the measurement axis after change. The same is also applied to a case of changing the numerical value range of the time axis or the numerical value range of the scale. In accordance with this arrangement, in case of enlarging or reducing the display of the time series graph, it is possible for the user to designate the middle value with an intuitive and easily recognizable operation.

For example, in case that the pH measurement result is calculated as a numerical value made to the third decimal place, it may be so set that a digit number of an effective digit is reduced by comparison with the pH measurement value by adjusting the middle value of the numerical value range of the scale to be the numerical value made to the second decimal place. An explanation will be provided with taking a case that the analog displaying screen is displayed as an example. In case that the mean value of the lower limit value and the upper limit value of the numerical value of the scale becomes 6.172, a numerical value 6.17 made to the second decimal place that is the closest to 6.172 is set as the mean value. The same is also applied to a case that the numerical value range of the measurement axis and the time axis of the graph displaying screen is changed.

Furthermore, in case that the display control part displays the graph displaying screen, when the user conducts the touch slide operation along the time axis or the measurement axis, the display control part releases only the automatic setting to the numerical value range of the coordinate axis to which the touch slide operation is conducted and keeps an automatic setting to the numerical value range of the other coordinate axis. However, it is not limited to this, and the automatic setting to both the numerical value range of the time axis and the numerical value range of the measurement axis may be released at a time when the user conducts the touch slide operation along the time axis and the measurement axis.

In addition, the user may conduct the touch slide operation by reversing the right and left directions or the top and bottom directions from those of the embodiment such that the display control part displays the past time series graph at a time when the user conducts the touch slide operation in the right direction. Furthermore, the display is of a single touch type that allows a position input of only a single point at once in the above-mentioned embodiment, however, the display may be of a multiple touch type that allows a position input of multiple points at once. The present claimed invention is not limited to each of the above-mentioned embodiments and a part or all of the above-mentioned embodiments may be appropriately combined within a range without departing from a spirit of the invention.

A second embodiment of this invention will be explained.

A conventional measurement device is a device separately comprising a display device that displays a value measured by each chemical measurement device and an operating part that switches a displaying mode of the display device or controls a movement of the measurement device (Patent document 1).

For this kind of the measurement device required is superior in design and easy to operate. In order to meet this demand, there is a measurement device using a touch panel type display that can integrate the display device with the operating part. More concretely, conventionally a physical switch to initiate a measurement is arranged separately from the screen, however, recently the switch is displaced by an icon displayed in the touch panel type display.

In case of a measurement device requiring complicated operations, if an input method is just by touching the icon with adopting the touch panel type display, there is a case that the user is difficult to operate the device intuitively. For example, in order to make it possible to conduct multiple kinds of operations such as correction, measurement and setting, it is necessary to configure a different screen for each operation and to make the screen having an arrangement with multiple-layer structure in view of eye friendliness. Then, in order to smoothly move from a layer where an operation can be conducted to a layer where another operation can be conducted, it is necessary for the operator to memorize a place where the icon locates or an order to operate the icon, which makes it difficult for the user to use the device intuitively.

In addition, if the user wants to know the measurement value displayed on the touch panel type display in detail, it is necessary to arbitrarily adjust a measurement range or a displayed interval. Also in this case, there is a case that the operation becomes complicated such that it is necessary for an input method of touching the icon to conduct the touch operations multiple times in accordance with an amount of enlarging or reducing amount.

Furthermore, in case that a function of operating the measurement device or an analysis function such as a graph or the like is further added, if the input method is only touching the icon, there is also a problem that the displaying screen becomes complicated so that the displaying screen is defiled because it is necessary to add the icon for each usage.

The second embodiment of this invention is to solve the above-mentioned problems and its object is to provide a measurement device that is superior in design as a whole by using a touch panel type display and that is easy to operate intuitively even though multiple kinds of input can be conducted.

The measurement device of this invention is a measurement device used for each chemical measurement and is characterized by comprising a touch panel type display on which an image is displayed and that can detect a touch slide operation by an operator, an input direction detection part that detects which direction the touch slide operation is input to among previously set multiple input receiving directions, a display control part that displays the image on the touch panel type display and that changes a displaying mode of the image in accordance with the direction of the touch slide operation detected by the input direction detection part, and a guide display part that further displays a guide indicating the input receiving direction on the image in case that the operator touches on the touch panel type display.

In accordance with this arrangement, since the guide display part indicates the input receiving direction on the image in case that the operator touches the touch panel type display, it is possible for the operator to intuitively understand which direction the touch slide operation is to be conducted in order to change the displaying mode of the displayed image. In addition, since the guide is not displayed while the display is not touched, there is no need of arranging, for example, the icon for operation on the screen on a constant basis so that it is possible to arrange other information such as the measurement value in a bigger image. Furthermore, since there is no need of newly adding an icon for operation, it is possible to prevent appearing complexity or troublesomeness of operation on the screen.

In addition, since the touch slide operation is received as the operation input, it is possible to intuitively conduct an operation such as turning a page by moving an image in a direction that is the same as that of the touch slide direction.

In order to make it possible to operate a lot of screens by a touch slide operation, it is preferable that the image has multiple displaying areas, the input receiving direction is set for each displaying area for the input direction detection part, and the guide display part displays the guide indicating the input receiving direction set in the displaying area touched by the operator.

In order to make it possible for the operator to intuitively understand how to operate the measurement device even though the image of the displaying mode can be changed in a mode different for each displaying area, it is preferable that the guide display part displays the guide indicating the input receiving direction set in the displaying area touched by the operator inside of the displaying area touched by the operator.

As a concrete embodiment to strengthen relevance between the change of the displaying mode of the image due to the touch slide operation and the guide and to make it possible for the operator to intuitively operate the measurement device, it is preferable that the multiple displaying areas comprises a measurement result displaying area that displays the measurement value measured by the chemical measurement and an peripheral area that displays information other than the measurement value measured by the chemical measurement, and the display control part changes the displaying mode of the measurement result displaying area alone in case that the input direction detection part detects the touch slide operation in the input receiving direction in the measurement result displaying area, and the display control part changes the displaying mode of whole of the image in case that the input direction detection part detects the touch slide operation in the input receiving direction in the peripheral area.

In accordance with the second embodiment of this invention, it is possible for a user to intuitively understand which direction the user conducts the touch slide operation in order to change the displaying mode of the displayed image. In addition, since it is so arranged that no guide displayed while the screen is not touched, a number of the operation button such as the icon does not increase even though various kinds of operations are set for the touch slide operation so that the designability or beauty of the screen display is easily improved.

A measurement device of the second embodiment will be explained in detail with reference to drawings. The measurement device 100 of the second embodiment has generally the same appearance as that of the measurement device shown in FIG. 1.

Figure 15:
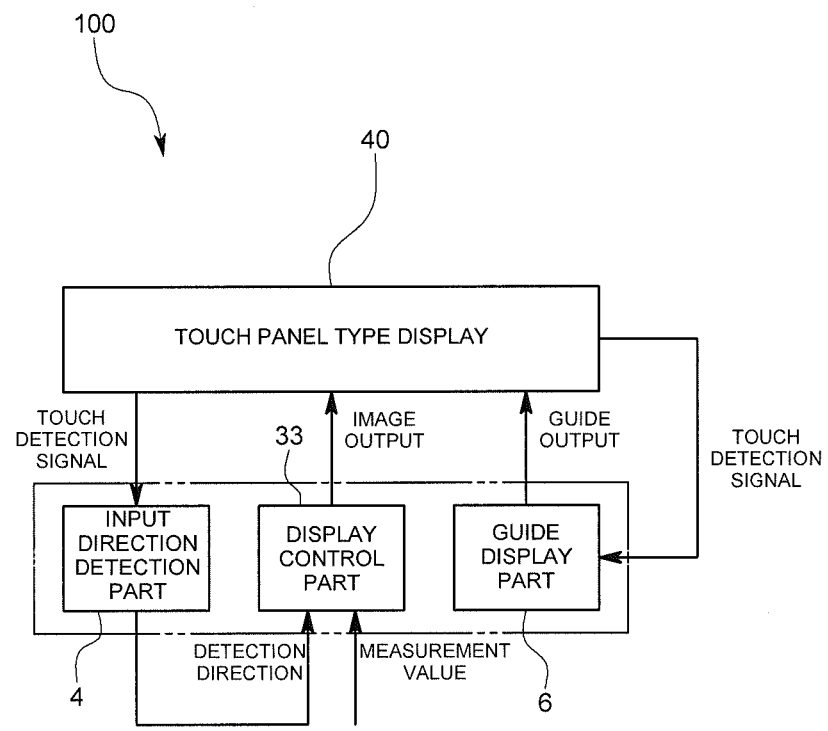
FIG. 15 is a function block diagram of a measurement device in accordance with a second embodiment of this invention.

The body 30 integrally comprises a CPU, an A/D converter, a memory and a touch panel type display 40 wherein an input/output device and a display are integrally formed as a hardware structure. And the CPU and its peripheral devices as needed are so arranged to produce functions at least as an input direction detection part 4, the display control part 33 and the guide display part 6 as shown by a function block diagram in FIG. 15 by working based on programs stored in the memory.

Each part will be explained.

The touch panel type display 40 is of a surface capacitive type and a single touch type. And the touch panel type display 40 is so arranged to be able to detect at least a touch operation and a touch slide operation. The touch operation in this embodiment is an operation corresponding to a click for a mouse and the touch slide operation in this embodiment is an operation corresponding to a drag for a mouse. In addition, the touch operation and the touch slide operation are conducted by directly touching the touch panel type display 40 with a hand or a finger of an operator, however, if other detecting method is used, the touch operation and the touch slide operation may be detected by the use of, for example, a pen or a stylus pen or the like.

The input direction detection part 4 is so arranged to detect an input direction of the touch slide operation based on the touch detection signal output from the touch panel type display 40 and to detect which direction the touch slide operation is input among previously set multiple input receiving directions. In other words, if the touch slide operation whose direction is other than the previously set directions is input, the input direction detection part 4 does not detect the touch slide operation as the touch slide operation. In addition, the input direction detection part 4 also detects a distance of the touch slide operation at a time when the touch slide operation is input, in addition to the input receiving direction.

The display control part 3 displays the above-mentioned image on the touch panel type display 40 and changes a displaying mode of the image in accordance with a direction of the touch slide operation detected by the input direction detection part 4.

In this second embodiment, the image displayed by the display control part 33 displays a pH measurement value, and at least includes a graph displaying screen W1 that displays the pH measurement value as a graph of a time series data, an analog displaying screen W2 that displays the pH measurement value in an analog meter display and a numerical value displaying screen W3 that displays a current value itself of the pH measurement value. Each screen is so arranged to be switched by the touch slide operation.

Each screen of the image has multiple displaying areas, and has a measurement result displaying area A1 that displays the pH measurement value, or the pH measurement value displayed in a graph or in an analog meter and a peripheral area A2 that is set to surround the measurement result displaying area A1 and that displays other information including, for example, a time and a date, an operation key displayed by each icon, an ambient temperature and an operation mode display or the like. Multiple input receiving directions are set for each displaying area and an operation at a time when the display control part 33 changes the displaying mode of the image is made to be different for each input receiving direction. In case that input of the touch slide operation in the input receiving direction is detected by the input direction detection part 4, a detail of an arrangement and an operation that the display control part 33 changes the displaying mode of the image will be explained together with an arrangement and an operation of the guide display part 6 to be described later. In addition, the measurement result displaying area A1 is indicated in an imaginary manner by a chain double-dashed line in drawings, however, the chain double-dashed line is not displayed on an actual screen.

Figure 16:
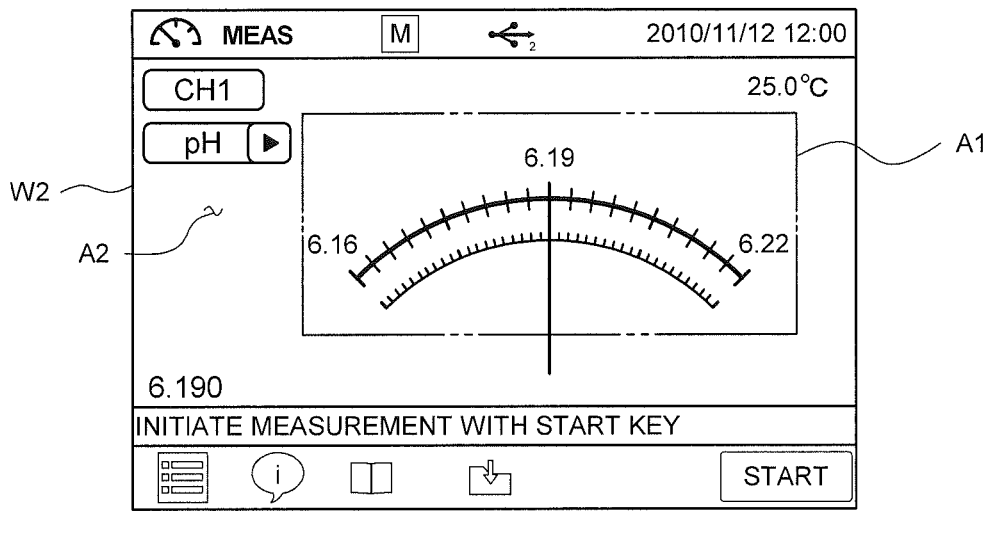
FIG. 16 is a pattern diagram showing a state that the analog displaying screen is touched and a state that the analog displaying screen is not touched in accordance with the second embodiment.
Figure 16:
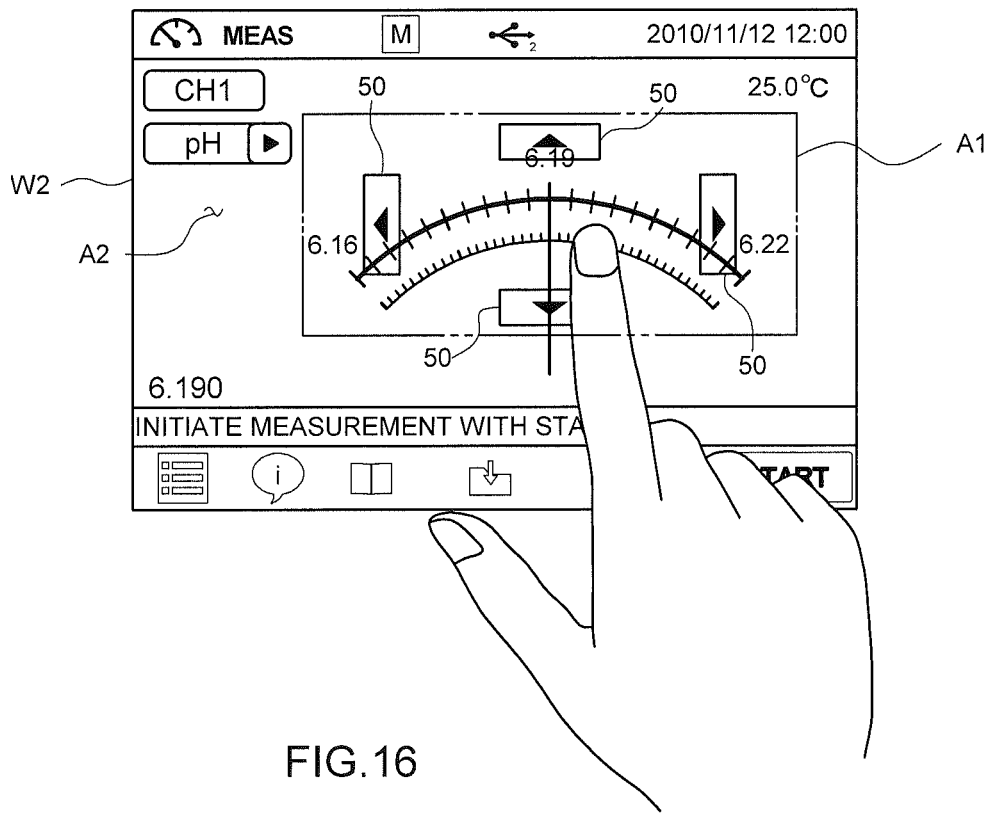

The guide display part 6 further displays the guide 50 indicating the input receiving direction on the image in case that the operator touches the touch panel type display 40. More concretely, the guide display part 6 displays the guide 50 so as to indicate only the input receiving direction set in the displaying area touched by the operator. A case that the above-mentioned image is the analog displaying screen W2 will be concretely explained as an example. FIG. 16(*a*) shows a state that the operator does not touch the touch panel type display 40. In case that the operator does not touch the touch panel type display 40, no guide 50 is displayed. When the operator touches the measurement result displaying area A1, the guide display part 6 displays the arrows as being the guide 50 indicating the direction to which the input receiving direction is set in the measurement result displaying area A1 as shown in FIG. 16 (b). In this embodiment, if the operator touches the measurement result displaying area A1 on the analog displaying screen W2 and the graph displaying screen W1, since the input receiving direction is previously set in four directions, namely, top, bottom, right and left, four arrows corresponding to each direction appear in the measurement result displaying area A1.

Next, a behavior of the display control part 33 in case that the touch slide operation is conducted in each input receiving direction in the measurement result displaying area A1 of the analog displaying screen W2 will be explained.

Figure 17:
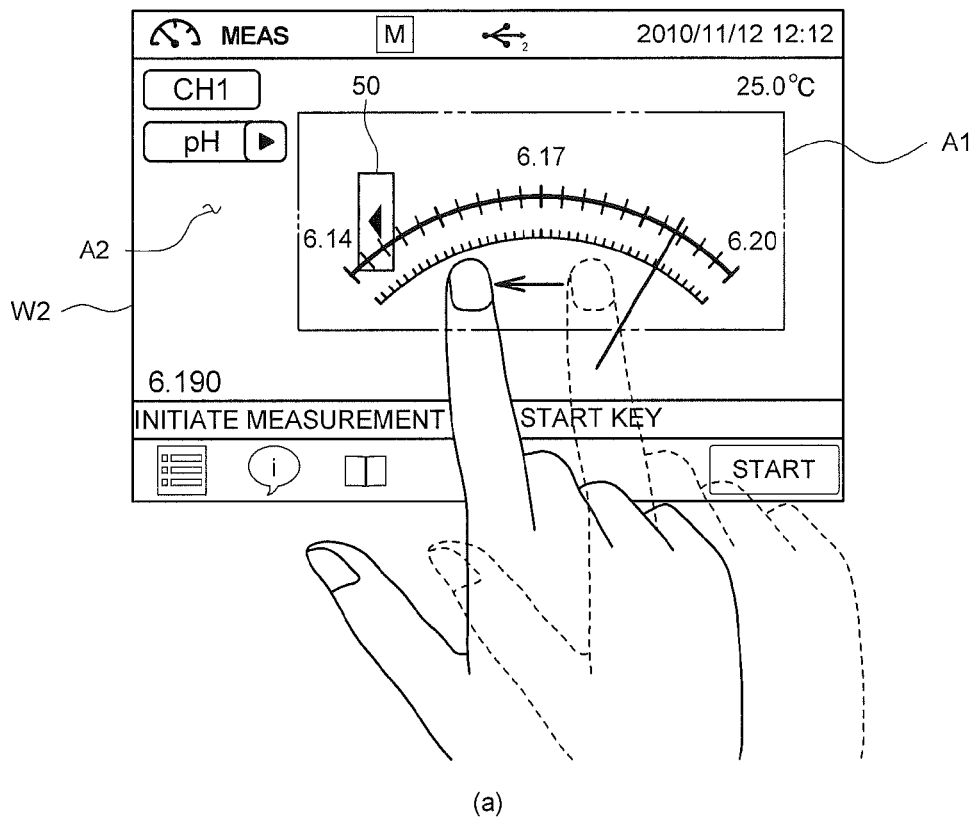
FIG. 17 is a pattern diagram showing a change at a time when a touch slide movement is input in the left direction and the right direction in the measurement result displaying area on the analog displaying screen in accordance with the second embodiment.
Figure 17:
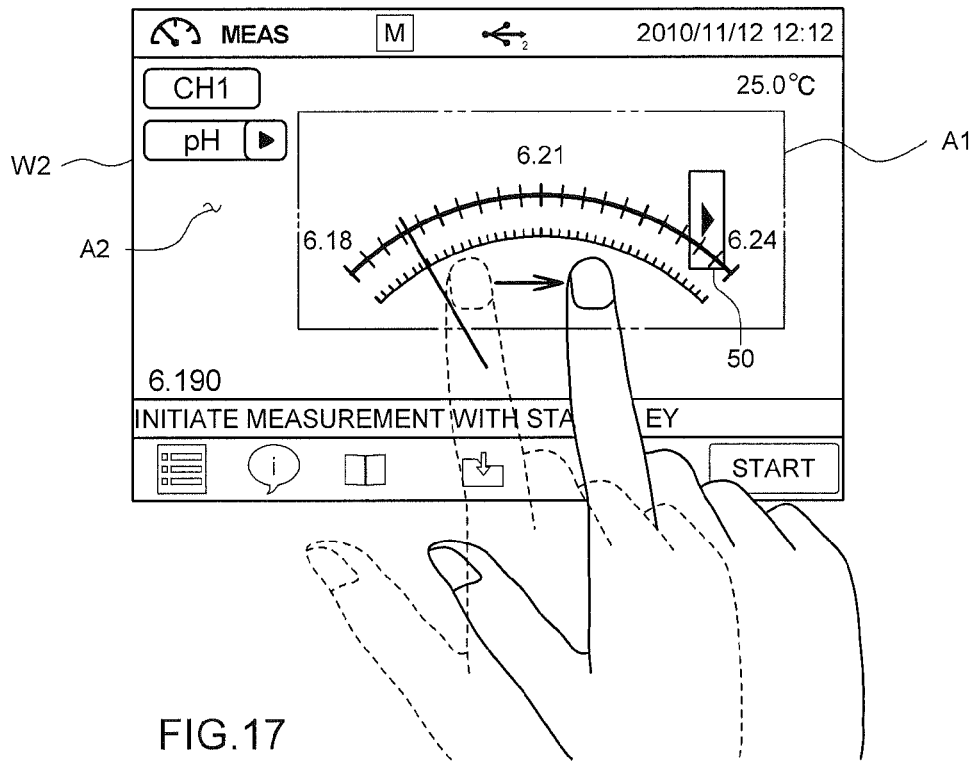

When the touch slide operation in the right and left directions are detected in the measurement result displaying area A1 as shown in FIG. 17, the display control part 33 is so arranged to change the numerical value range of the analog meter. More concretely, when the touch slide operation in the left direction is detected by the input direction detection part 4 as shown in FIG. 17 (a), the display control part 33 changes the numerical value displaying range so as to decrease the maximum displaying value and the minimum displaying value by a predetermined amount with keeping a range of the analog meter and a unit for every scale. Contrary, when the touch slide operation in the right direction is detected by the input direction detection part 4 as shown in FIG. 17 (b), the display control part 33 changes the numerical value displaying range so as to increase the maximum displaying value and the minimum displaying value by a predetermined amount with keeping the range of the analog meter and the unit for every scale.

Figure 18:
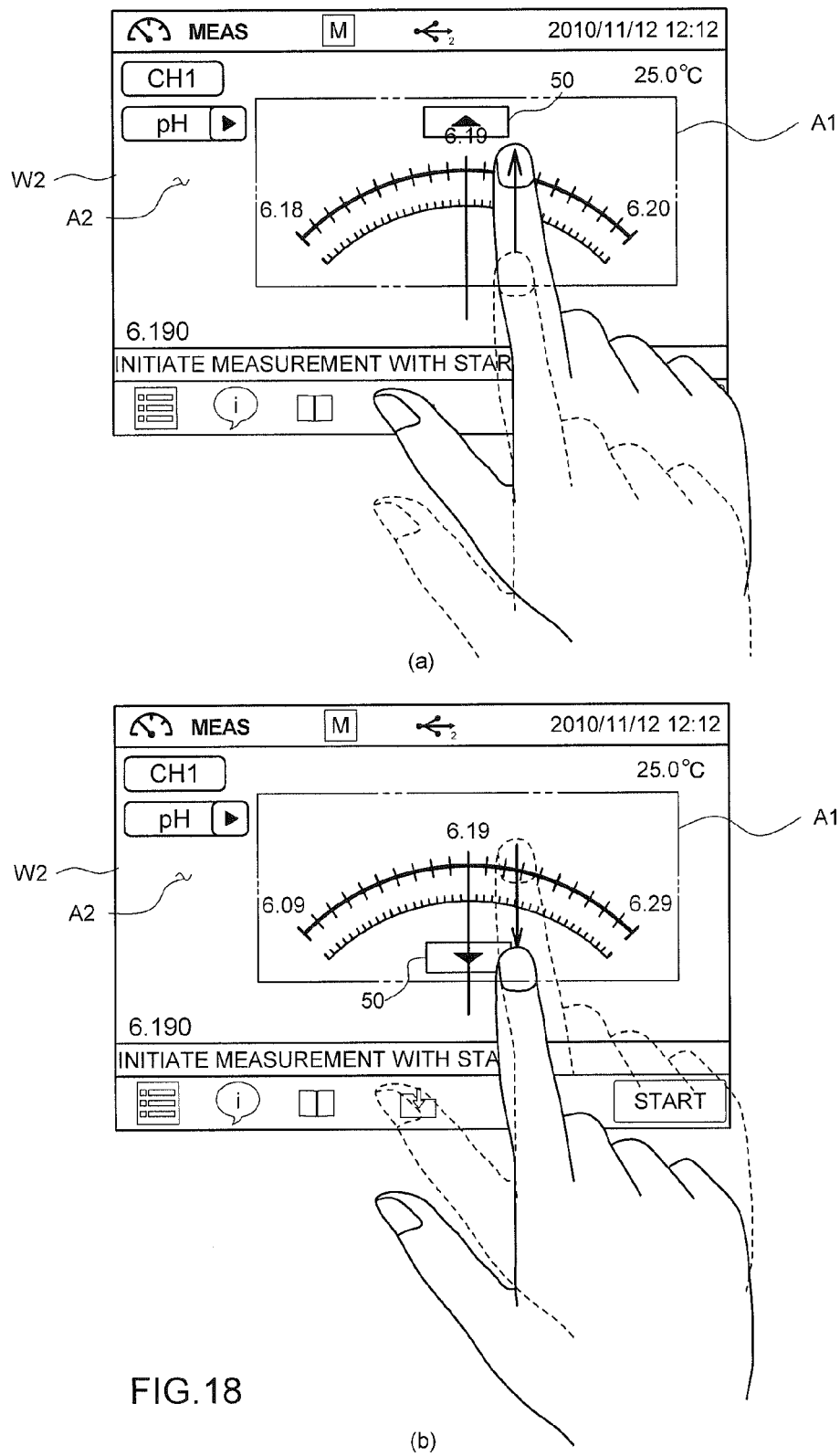
FIG. 18 is a pattern diagram showing a change at a time when a touch slide movement is input in the upper direction and the bottom direction in the measurement result displaying area on the analog displaying screen in accordance with the second embodiment.

Meanwhile, when the touch slide operation in the top or bottom direction is detected in the measurement result displaying area A1 as shown in FIG. 18, the display control part 33 changes and displays a variation of one tick of the scale with keeping the middle value of the analog meter. More concretely, in case that the touch slide operation is input in the top direction as shown in FIG. 18 (a), the display control part 33 reduces the variation of one tick of the scale of the analog meter. Contrarily, in case that the touch slide operation is input in the bottom direction as shown in FIG. 18 (b), the display control part 33 increases the variation of one tick of the scale.

Figure 19:
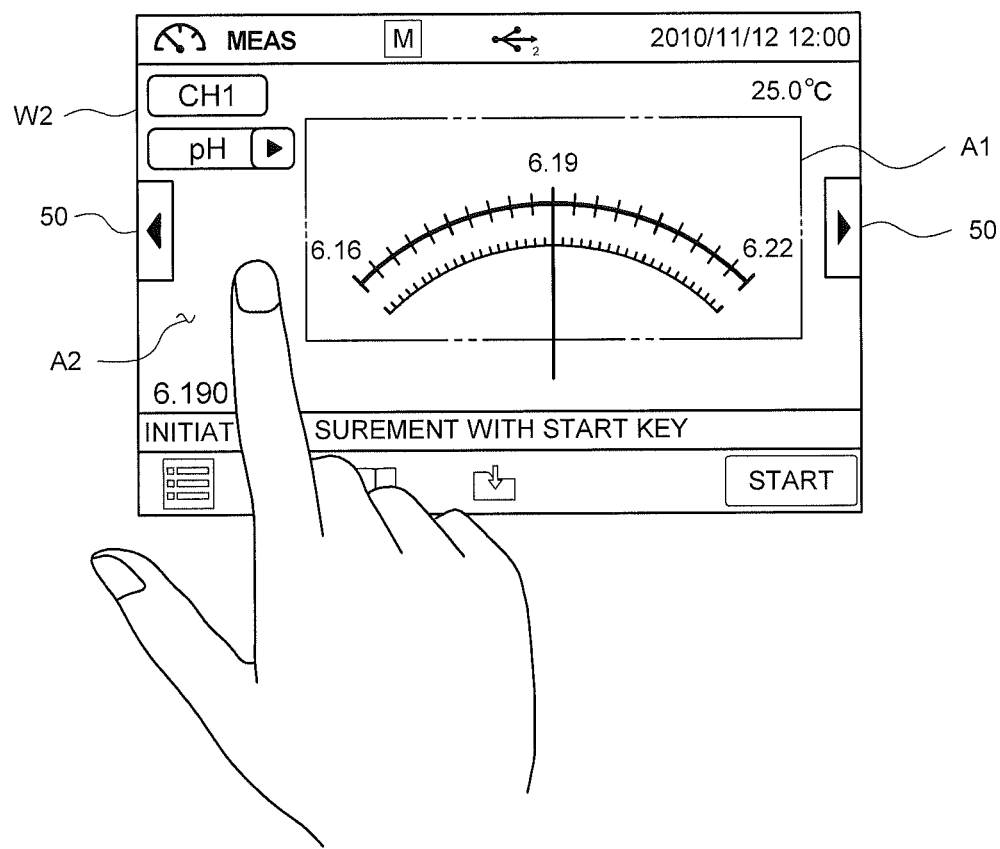
FIG. 19 is a pattern diagram showing a state wherein an peripheral area is touched on the analog displaying screen in accordance with the second embodiment.

In addition, when the operator touches the above-mentioned peripheral area A2 as shown in FIG. 19, the guide 50 is displayed at the right and left ends of the touch panel type display 40. In this embodiment, since the input receiving direction is set in the right and left directions only in the peripheral area A2, only two arrows are displayed for the input direction detection part 4 by the guide display part 6.

More concretely, in case that the touch slide operation in the left direction in the peripheral area A2 of the analog displaying screen W2 is detected, the display control part 33 moves the analog displaying screen W2 in the left side of the screen and displays the numerical value displaying screen W3 by entering the left end of the numerical value displaying screen W3 from the right end of the screen in sequence with moving the analog displaying screen W2 to go out from the left end of the screen in sequence not to be displayed. Reversely, in case that the touch slide operation in the right direction in the peripheral area A2 is detected, the display control part 33 moves the analog displaying screen W2 in the right side of the screen and displays the graph displaying screen W1 by entering the right end of the graph displaying screen W1 from the left end of the screen in sequence with moving the analog displaying screen W2 to go out from the right end of the screen in sequence not to be displayed.

In accordance with the measurement device 100 of the second embodiment having the above-mentioned arrangement, since the guide display part 6 further displays the guide 50 that indicates the direction to which the touch slide operation is to be input on the image at a time when the displaying area is touched, it is possible for the operator to easily infer how to operate the measurement device without a specific explanation in order to change the screen display. As a result of this, even though the operator uses the measurement device for the first time, it is possible for the operator to understand how to operate the measurement device intuitively.

In addition, since the guide 50 is not displayed while the displaying area is not touched, it is possible not to make the screen crowded with the operation guides 50 even though the multiple operations are set in the displaying area.

In other words, conventionally if multiple operations are set for each displaying area so as to be multi-function, the screen configuration is complicated and its designability also becomes retarded. However, in accordance with the measurement device 100 of this embodiment, it is possible to allow many different kinds of operations and to satisfy both user-friendliness and designability due to an effect resulting from the guide display part 6.

Other embodiment of the second embodiment will be explained.

The input receiving direction is set in either of the top and bottom directions or the right and left directions in the second embodiment, however, the input receiving direction may be set in other direction. Concretely, the input receiving direction may be set in an oblique direction. In addition, the touch panel type display uses a single touch type in the above embodiment, however, it may be, for example, a double touch type. In this case, when the double touch is detected by the touch panel type display, the guide display part may display a guide to urge an input in two directions simultaneously. For example, the guide to urge a touch slide operation of rotation or a touch slide operation of two different directions may be displayed. Furthermore, the guide display part indicates the input receiving direction that is previously set as the guide by the use of the arrow in the second embodiment, however, the guide function may be produced by other notation. For example, the guide may display a content of the movement after operation by a graphic display or a word together with the arrow.

Two displaying areas are set in the second embodiment, however, one displaying area or further more displaying areas may be set. In addition, a change amount of the displaying range of the graph or the analog meter may be changed in proportion to the input distance input by the touch slide operation. A speed of switching the screen may be changed in accordance with the input distance.

The portable measurement device is explained as the example in the second embodiment, however, this invention may be used for a stationary measurement device.

Various modifications or the embodiments may be combined without departing from the spirit of this invention.

POSSIBLE APPLICATIONS IN INDUSTRY

As mentioned, in accordance with this invention, it is possible for the user to switch the displaying screen by the intuitive and easily recognizable operation so that the user can conduct the switch operation with ease by verifying the displaying screen after switch in the middle of the switching operation.

In addition, in accordance with this invention, it is possible for the user to intuitively understand which direction the user conducts the touch slide operation in order to change the displaying mode of the displayed image. In addition, since it is so arranged that no guide is displayed while the screen is not touched, a number of the operation button such as the icon does not increase even though various kinds of operations are set for the touch slide operation so that the designability or beauty of the screen display is easily improved.

The invention claimed is:

1. A measurement device for use with an object to be measured, the measurement device comprising:
   a probe;
   a display;
   a display control part configured to display, on the display, a measurement result obtained by the probe that measures at least either one of a pH, an oxidation-reduction potential, an ionic concentration and electric conductivity by making contact with the object to measured, wherein
   the display control part displays displaying screens in a switchable manner, the displaying screens comprising:
      a numerical value displaying screen that displays the measurement result as a numerical value,
      an analog displaying screen that displays a series of a scale on a predetermined position of which a value is assigned and an indication device that indicates a position corresponding to the measurement result on the scale, and
      a graph displaying screen that displays the measurement result as a time series graph on a coordinate system where one axis indicates a time and the other axis indicates the measurement result,
   the display is a touch panel type display,
   the display control part is configured to switch each of the displaying screens continuously in conjunction with a touch slide operation on the display by moving a first displaying screen of the two displaying screens to the outside of a displaying area on the display and by moving a second displaying screen of the displaying screens to the inside of the displaying area in a manner such that the first displaying screen and the second displaying screen do not overlap, and
   the display control part is configured to display, in the middle of the switching displaying screens and in the displaying area at the same time:
      the numerical value as the measurement result of the numerical value displaying screen and the series of the scale of the analog displaying screen; or
      the numerical value as the measurement result of the numerical value displaying screen and the time series graph of the graph displaying screen.

2. The measurement device described in claim 1, wherein in case that a sliding distance of the touch slide operation is a predetermined value or more, the display control part displays the other displaying screen, and
in case that the sliding distance of the touch slide operation is less than the predetermined value, the display control part displays the displaying screen that has been displayed prior to the touch slide operation.

3. The measurement device described in claim 1, wherein in case that the touch operation is conducted on the display, the display control part displays a guide indicating a direction to which the displaying screen is movable.

4. The measurement device described in claim 1, wherein in the middle of the switching screens, a part of the numerical value of the numerical displaying screen and the series of the scale of the analog displaying screen, or, a part of the numerical value of the numerical displaying screen and the time series graph of the graph displaying screen is displayed in the displaying area at the same time.

* * * * *